(12) United States Patent
Ide et al.

(10) Patent No.: US 8,883,969 B2
(45) Date of Patent: Nov. 11, 2014

(54) METHOD FOR PRODUCTION OF CAROTENOID-SYNTHESIZING MICROORGANISM AND METHOD FOR PRODUCTION OF CAROTENOID

(75) Inventors: Teruhiko Ide, Tokyo (JP); Toru Tanaka, Kanagawa (JP)

(73) Assignee: Tosoh Corporation, Shunan-shi (JP)

(*) Notice: Subject to any disclaimer, the term of this patent is extended or adjusted under 35 U.S.C. 154(b) by 1291 days.

(21) Appl. No.: 12/089,486

(22) PCT Filed: Sep. 25, 2006

(86) PCT No.: PCT/JP2006/318904
§ 371 (c)(1),
(2), (4) Date: Jul. 1, 2008

(87) PCT Pub. No.: WO2007/049416
PCT Pub. Date: May 3, 2007

(65) Prior Publication Data
US 2009/0226582 A1 Sep. 10, 2009

(30) Foreign Application Priority Data
Oct. 28, 2005 (JP) .................. 2005-315070

(51) Int. Cl.
*C07K 14/00* (2006.01)
*A23L 1/275* (2006.01)
*C12P 23/00* (2006.01)
*A23K 1/16* (2006.01)
*C12N 15/74* (2006.01)

(52) U.S. Cl.
CPC ............. *C12P 23/00* (2013.01); *A23L 1/2753* (2013.01); *A23K 1/1606* (2013.01); *C12N 15/743* (2013.01)
USPC ........................................... 530/350

(58) Field of Classification Search
CPC ........ C12P 23/00; C12N 15/743; C07H 21/02
See application file for complete search history.

(56) References Cited

U.S. PATENT DOCUMENTS 5,811,273 A * 9/1998 Misawa et al. .............. 435/148
2005/0124033 A1 * 6/2005 Sharpe et al. ................ 435/67

FOREIGN PATENT DOCUMENTS

WO 2004 087892 10/2004

OTHER PUBLICATIONS

Misawa, Norihiko et al., "Structure and Functional Analysis of a Marine Bacterial Carotenoid Biosynthesis Gene Cluster and Astaxanthin Biosynthetic Pathway Proposed at the Gene Level", Journal of Bacteriology, vol. 177, No. 22, pp. 6575-6584, (1995).
Simon, R. et al., "A broad Host Range Mobilization System for in Vivo Genetic Engineering: Transposon Mutagenesis in Gram Negative Bacteria", Bio/Technology, vol. 1, No. 9, pp. 784-791, (1983).
Van Laethem, Y. et al., "Serum Bactericidal Activity of Aztreonam, Cefoperazone, and Amikacin, Alone or in Combination, Against *Escherichia coli, Klebsiella pneumoniae, Serratia marcescens,* and *Pseudomonas aeruginosa*", Antimicrobial Agents and Chemotherapy, vol. 26, No. 2, pp. 224-227, (1984).
"Flavobacterium ATCC21588 geranylgeranyl synthase (crtE), phytoene synthase (crtB), phytoene desaturase (crtI), lycopene cyclase (crtY), b-carotene hydroxylase (crtZ) genes, complete cds", Database EMBL [Online], XP002544048, retrieved from EBI accession No. EMBL: U62808, Feb. 20, 1997, pp. 1-4.
Kim Young Tae, et al., "Isolation and characterization of carotenoid biosynthesis gene cluster from marine bacterium *Paracoccus haeundaensis*", Database Biosis [Online], Biosciences Information Service, XP002544049, Database accession No. PREV200510185178, May 2004, pp. 1-2, (abstract).
Markus Hümbelin, et al., "Genetics of isoprenoid biosynthesis in *Paracoccus zeaxanthinifaciens*", Gene, XP004388023, Sep. 4, 2002, pp. 129-139.
Jae Hyung Lee, et al, "Functional expression of the astaxanthin biosynthesis genes from a marine bacterium, *Paracoccus haeundaensis*", Biotechnology Letters, XP019391559, vol. 28, No. 15, Jun. 24, 2006, pp. 1167-1173.
U.S. Appl. No. 12/089,451, filed Apr. 7, 2008, Tanaka, et al.
Qoronfleh, et al. "Identification and Characterization of Novel Low-Temperature-Inducible Promoters of *Escherichia coli*." Journal of Bacteriology, vol. 174, No. 24. Dec. 1992. pp. 7902-7909.
"*Paracoccus* sp. N81106 crtW, crtZ, crtY, crtI, crtB genes, complete cds.", Database EMBL [Online], retrieved from EBI accession No. EMBL: D58420, Jan. 3, 1996, 4 pages.
Norihiko Misawa, et al., "Canthaxanthin Biosynthesis by the Conversion of Methylene to Keto Groups in a Hydrocarbon β-Carotene by a Single Gene", Biochemical and Biophysical Research Communications, vol. 209, No. 3, XP602246A, Apr. 26, 1995, pp. 867-876.

* cited by examiner

*Primary Examiner* — Michele K Joike
(74) *Attorney, Agent, or Firm* — Oblon, Spivak, McClelland, Maier & Neustadt, L.L.P.

(57) ABSTRACT

A method for producing a carotenoid comprising the steps of cultivating a cell transformed with a DNA sequence comprising a DNA sequence depicted in anyone of SEQ ID NOs: 2-7 or a cell transformed with a vector having a DNA sequence depicted in anyone of SEQ ID NOs: 2-7 under proper culture conditions and isolating the carotenoid from the cell or the culture.

14 Claims, 8 Drawing Sheets

METHOD FOR PRODUCTION OF CAROTENOID-SYNTHESIZING MICROORGANISM AND METHOD FOR PRODUCTION OF CAROTENOID

CROSS-REFERENCE TO RELATED APPLICATIONS

The present application is a 35 U.S.C. §371 National Stage patent application of International patent application PCT/JP06/318904, filed on Sep. 25, 2006, which claims priority to Japanese patent application JP 2005-315070, filed on Oct. 28, 2005.

TECHNICAL FIELD

The present invention relates to a method of preparing a carotenoid synthesizing microorganism and a method of producing carotenoids.

BACKGROUND ART

The present invention relates to DNA chains which are useful for synthesis of carotenoids suitably used for reviving the colors of farm-raised fish such as sea bream, shrimp and salmon, and hen eggs, and for synthesis of carotenoids such as astaxanthin which is applicable as a coloring agent or antioxidant to foods, and to methods of producing carotenoids such as astaxanthin utilizing microorganisms incorporating such DNA chains.

In the natural word, over 600 of different carotenoids have been identified from plants, microorganisms and the like. Industrially useful carotenoids are generally produced by chemical synthesis processes for which possibility of undesired actions such as contamination of synthesis auxiliary materials is feared. In addition, tastes of consumers tend to lean toward naturally-occurring carotenoids. However, there is a limit to extraction from plants and the like natural products, and an effective industrial process is not entirely established. As a production method of naturally-occurring carotenoids, microbial fermentation methods have been reported in some cases, however, none of such cases enable production of carotenoids in an amount which is enough for economical industrial production. Likewise the cases of carotenoids, when trying to produce a functional substance from a microorganism, one will choose a microorganism which serves as a host of fermentation by broad screening. Then, in many cases, through classical mutation and breeding using a chemical treatment agent, a highly productive strain is isolated and subjected to production or research, because a production amount from a wild-type of carotenoid producing microorganism is usually small.

As a microorganism that produces useful carotenoid, Yokoyama et al. reported *Agrobacterium* (later, reclassified into bacteria belonging to *Paracoccus*) marine bacteria (Non-patent document 1). These strains are characterized by synthesizing astaxanthin which is a functional carotenoid in high content. As described above, a production amount of astaxanthin or the like of *Paracoccus* bacterial can be increased through mutation process, and a strain TSN18E7 with improved production amount (see Japanese Patent Laid-Open Publication 2005-58216) is deposited to International Patent Organism Depositary, National Institute of Advanced Industrial Science and Technology under the number of FERM P-19746.

A carotenoid biosynthesis pathway is made up of various enzymes, and genes encoding such enzymes have been analyzed by many researches. In a typical pathway, for example, carotenoid is synthesized in its early stage by an isoprenoid biosynthesis pathway which is shared by steroid and terpenoid, starting from mevalonic acid which is a basic metabolite. Farnesyl pyrophosphate having 15 carbons (C15) generating through the isoprenoid basic synthesis system is condensed with isopentenyl diphosphate (IPP) (C5), to give geranylgeranyl diphosphate (GGPP) (C20). Then through condensation of two molecules of GGPP, colorless phytoene which is the first carotenoid is synthesized. The phytoene is then converted into lycopene through a series of unsaturation reactions, and then the lycopene is converted into β-carotene through a cyclization reaction. Then, a hydroxyl group and a keto group are introduced into the β-carotene, which leads synthesis of various xanthophylls represented by astaxanthin (FIG. 1).

From these gene level findings, studies intended to improvement of carotenoid synthesis with the use of genetic recombination technique have been made. See Chia-wei Wang et al., Biotechnol. Prog., 16: 922-926 (2000); Claudia Schmidt-Dannert et al., Nat. Biotechnol., 18: 750-753 (2000); Daisuke Umeno et al., Appl. Environ. Microbiol., 69: 3573-3579 (2003), for example. In these studies, *Escherichia coli* that does not synthesize carotenoid is used as a host, so that it would be difficult to apply these studies to industrial production because of their low productivity of carotenoid. In other report, increase in carotenoid synthesis amount is realized by introducing a carotenoid gene into a bacterium that produces carotenoid (Patent document 1). However, it would be still difficult to apply such prepared gene recombinant strain to industrial production because of its low amount of carotenoid synthesis.

[Non-patent document 1] Yokoyama, A. H. Izumida, and W. Miki, Production of astaxanthin and 4-ketozeaxanthin by the marine bacterium, *Agrobacterium aurantiacum*, Biosci. Biotechnol. Biochem., 58: 1842-1844 (1994).

[Non-patent document 2] Norihiko Misawa, Yoshiko Satomi, Keiji Kondo, Akihiro Yokoyama, Susumu Kajiwara, Tochiko Saito, Takeshi Ohtani, and Wataru Miki, Structure and functional analysis of a marine bacterial carotenoid biosynthesis gene cluster and astaxanthin biosynthetic pathway proposed at the gene level, J., Bacteriology 177: 6575-6584 (1995).

[Non-patent document 3] Eric A. Johnson, and William A. Schroeder, Microbial Carotenoids, Advances in Biochemical Engineering Biotechnology, 53: 119-178 (1995).

[Non-patent document 4] P. C. Lee, and Schmidt-Dannert, Metabolic engineering towards biotechnological production of carotenoids in microorganism, 60:1-11 (2002).

[Non-patent document 5] Kovach, M. E. et al., GENE166, 175-176 (1995).

[Non-patent document 6] R. Simon, U. Priefer, and A. Puhler, A broad host range mobilization system for in vivo genetic engineering: transposon mutagenesis in gram negative bacteria, BIO/TECHNOLOGY, 1: 784-791 (1983).

[Non-patent document 7] Cedric Y. Szpiper, Michel Faelen, and Martine Couturier, Mobilization function of the pBHR1 plasmid, a derivative of the broad-host-range plasmid pBBR1, J. Bacteriology, 183: 2101-2110 (2001).

[Patent document 1] Japanese translation of PCT application JP-A 2004-527265

[Patent document 2] Japanese Patent Publication No. 3403381

[Patent document 3] Japanese Patent Application No. 2005-106045

SUMMARY OF THE INVENTION

Means to be Solved by the Invention

It is an object of the present invention to prepare a microorganism which allows carotenoid production in industrial production scale. It is also an object of the present invention to produce carotenoids using a novel carotenoid producing strain and to provide the carotenoids.

Means for Solving the Problem

Through diligent efforts for solving the aforementioned problems, the present inventors found that a synthesis amount of carotenoid is increased by cloning a carotenoid synthesis gene of *Paracoccus* sp. strain MBIC1143 which is a carotenoid synthesis bacterium; recombining the carotenoid synthesis gene into an appropriate plasmid vector; introducing the plasmid vector harboring the carotenoid synthesis gene inserted therein into a wild-type strain, a mutant strain with increased carotenoid synthesis ability as a result of mutation treatment, or a carotenoid synthesis tolerant strain of *Paracoccus* sp. by a gene transduction technique such as conjugational transfer; and letting a carotenoid synthase encoded by the carotenoid synthesis gene express.

In other words, the present inventors found that a carotenoid content such as astaxanthin is dramatically increased by introducing into *Paracoccus* sp. strain MBIC1143, a DNA chain selected from the group consisting of (a) DNA chain encoding a polypeptide having such an enzymatic activity that converts a methylene group at 4 position in β-ionone ring into a keto group (crtW), (b) DNA chain encoding a polypeptide having such an enzymatic activity that adds one hydroxyl group to a carbon at 3-position of 4-keto-β-ionone ring and/or at 3-position of β-ionone ring (crtZ), (c) DNA chain encoding a polypeptide having such an enzymatic activity that converts lycopene into β-carotene (crtY) (d) DNA chain encoding a polypeptide having such an enzymatic activity that converts phytoene into lycopene (crtI), (e) DNA chain encoding a polypeptide having prephytoene synthase activity (crtB), and (f) DNA chain encoding a polypeptide having geranylgeranyl diphosphate synthase activity (crtE), and completed the present invention.

(1) A method of increasing generation of carotenoid, wherein a DNA chain selected from the group consisting of the (a), (b), (c), (d), (e) and (f) is introduced into a carotenoid producing microorganism such as *Paracoccus* sp., and the resultant transformed microorganism is cultured in a culture medium.

(2) The method of increasing generation of carotenoid according to (1), wherein the polypeptide having a carotenoid synthesis activity is a polypeptide of (i) or (ii) below.
(i) Polypeptide having an amino acid sequence represented by SEQ ID NO: 2, 3, 4, 5, 6 or 7.
(ii) Polypeptide having an amino acid sequence which is substantially homologous to an amino acid sequence represented by SEQ ID NO: 2, 3, 4, 5, 6 or 7.

The present invention also relates to carotenoid producing methods of (3) to (4) below.

(3) A method of producing a carotenoid, wherein a DNA chain selected from the group consisting of the (a), (b), (c), (d), (e) and (f) is introduced into a carotenoid producing microorganism such as *Paracoccus* sp., and the resultant transformed microorganism is cultured in a culture medium.

(4) The method of producing carotenoid according to (3), wherein the polypeptide having a carotenoid synthesis activity is a polypeptide of (i) or (ii) below.
(i) Polypeptide having an amino acid sequence represented by SEQ ID NO: 2, 3, 4, 5, 6 or 7.
(ii) Polypeptide having an amino acid sequence which is substantially homologous to an amino acid sequence represented by SEQ ID NO: 2, 3, 4, 5, 6 or 7.

The present invention also relates to a transformation method, wherein a DNA chain selected from the group consisting of the above (a), (b), (c), (d), (e) and (f) or a plasmid vector having the DNA chain inserted therein is introduced into a carotenoid producing microorganism such as *Paracoccus* sp. The present invention also relates to a microorganism having improved carotenoid productivity by introducing a plasmid into a cell, of which cell growth is not influenced by the replication of the plasmid occurring in a cell by the introducing a plasmid vector, and/or by carotenoids produced by carotenoid synthesis gene encoded by the plasmid

Effect of the Invention

According to the present invention, there are provided a DNA chain which significantly improves a production amount in biosynthesis of carotenoid by microorganism, and a method which involves introduction of the DNA chain into a carotenoid producing microorganism and expression thereof, thereby increasing an amount of carotenoid produced by the microorganism several times.

BEST MODE FOR CARRYING OUT THE INVENTION

In the following, the present invention will be described in detail.

As is described in detail in the section of "conventional art", microorganisms such as *Escherichia coli* are enabled to produce useful carotenoids such as astaxanthin, zeaxanthin, β-carotene and lycopene as a result of introduction of carotenoid biosynthesis gene from carotenoid producing bacteria such as marine bacteria *Paracoccus* sp. and the like. On the other hand, in order to compete with costs of organic synthesis methods, it is necessary to increase a production amount of carotenoid as much as possible. The DNA chain of the present invention is selected from the group consisting of (a) DNA chain encoding a polypeptide having such an enzymatic activity that converts a methylene group at 4 position in β-ionone ring into a keto group (crtW), (b) DNA chain encoding a polypeptide having such an enzymatic activity that adds one hydroxyl group to a carbon at 3-position of 4-keto-β-ionone ring and/or at 3-position of β-ionone ring (crtZ), (c) DNA chain encoding a polypeptide having such an enzymatic activity that converts lycopene into β-carotene (crtY), (d) DNA chain encoding a polypeptide having such an enzymatic activity that converts phytoene into lycopene (crtI), (e) DNA chain encoding a polypeptide having prephytoene synthase activity (crtB), and (f) DNA chain encoding a polypeptide having geranylgeranyl diphosphate synthase activity (crtE), and is extremely useful for increasing a production amount of carotenoid, in particular, astaxanthin. By raising an expression level of gene of enzyme or the like through current advanced genetic engineering techniques, a production amount of a protein encoded by the gene can be increased relatively easily. In metabolic concept, there is a report that introduction of IPP isomerase gene located on upstream side of the carotenoid synthesis system significantly increases production of carotenoid in an expression cell (Patent document 2). The success in increasing a carotenoid production amount by introduction of IPP isomerase gene is attributed to the fact that the upstream metabolic pathway up to FPP (FIG.

1) is broadened by the introduction, resulting in increase in supply amount of FPP and hence increase in amount of carotenoid.

However, keeping the production of carotenoid, in particular, of astaxanthin which is one of the objects of the present invention in mind, subsequent metabolic reactions will not proceed only by the upstream gene, so that metabolic intermediates such as β-carotene accumulate, and a sufficient production amount is not obtained. In other words, it is important to increase the amount of astaxanthin in a total amount of carotenoids including lycopene, β-carotene, echinenone, β-cryptoxanthin, 3'-hydroxyechinenone, zeaxanthin, 3-hydroxyechinenone, canthaxanthin, phonicoxanthin, 4-ketozeaxanthin which are intermediates of astaxanthin synthesis, and astaxanthin and so on. The present inventors found that a sufficient amount of astaxanthin is synthesized without accumulation of metabolic intermediates in expression cells when a DNA chain selected from the group consisting of the above (a), (b), (c), (d), (e) and (f) is introduced rather than using IPP isomerase, for sufficiently producing astaxanthin without stopping at metabolic intermediates of astaxanthin. The present inventors also considered that introduction of DNA chain of (f) is effective for increasing carotenoid. In other words, based on a comparable idea to that for increase in expression amount by introduction of IPP isomerase, the present inventors found that by introducing a DNA chain encoding geranylgeranyl diphosphate synthase which is considered as an upstream synthase according to metabolic concept, an expression amount of geranylgeranyl diphosphate synthase increases, and geranylgeranyl diphosphate which is a product is supplied to the to the carotenoid metabolic system, and thus a total carotenoid amount is increased by a series of carotenoid synthases. Accordingly, combination of a DNA chain selected from (a), (b), (c), (d) and (e) and a DNA chain of (f) dramatically increases a synthesis amount of astaxanthin. Furthermore, the present inventors found that combination of DNA chains of (a), (b), (c), (d), (e) and (f) enables selective synthesis of desired carotenoid. For example, for selective synthesis of β-carotene, (c), (d) and (e) may be combined, and (f) may be further combined for increasing the production amount. For selective synthesis of zeaxanthin, (b), (c), (d) and (e) may be combined, and (f) may be further combined for increasing the production amount. For selective synthesis of lycopene, (d) and (e) may be combined, and (f) may be further combined for increasing the production amount. If a combination of (a) and (b) is available, oxidation of β-carotene selectively proceeds, which enables astaxanthin to be efficiently and selectively synthesized. In order to further increase the production amount of astaxanthin, combinations of (d), (e) and (f) may be used.

In the present invention, when referring to a combination of DNA chains, the DNA chains may be individually used, however they may be genetically coupled serially. The combination number to be coupled can be selected such that a desired function is maximum in the combination. When DNA chains are individually used, they may be inserted into an appropriate plasmid vector. Plasmid vectors should merely function in a host cell into which the plasmid vector is introduced, and an appropriate plasmid vector may be used singly or plural kinds of plasmid vectors may be used insofar as they are not subjected to compatibility restraint.

In the present invention, the term "carotenoid" includes phytoene, lycopene, β-carotene, zeaxanthin, canthaxanthin, astaxanthin, adonixanthin, cryptoxanthin, echinenone, adonirubin, and combinations thereof. Preferably, it is astaxanthin.

Specifically, the present invention provides a DNA chain having a property of increasing a production amount of carotenoid, in particular, astaxanthin, which is selected from the group consisting of a DNA chain encoding a polypeptide having such an enzymatic activity that converts a methylene group at 4 position in β-ionone ring into a keto group (crtW), a DNA chain encoding a polypeptide having such an enzymatic activity that adds one hydroxyl group to a carbon at 3-position of 4-keto-β-ionone ring and/or at 3-position of β-ionone ring (crtZ), a DNA chain encoding a polypeptide having such an enzymatic activity that converts lycopene into β-carotene (crtY), a DNA chain encoding a polypeptide having such an enzymatic activity that converts phytoene into lycopene (crtI), a DNA chain encoding a polypeptide having prephytoene synthase activity (crtB), and a DNA chain encoding a polypeptide having geranylgeranyl diphosphate synthase activity (crtE), and a method of producing carotenoid which comprises introducing the above DNA chain into a carotenoid producing microorganism and culturing the transformed microorganism in a culture medium to thereby increase a carotenoid content of the culture.

In another aspect of the present invention, the present invention relates to a method of preparing a carotenoid producing cell. The method comprises the steps of: introducing a DNA chain, that encodes an enzyme involved in a series of carotenoid synthesis expressed in a cell, into the cell; and preparing and selecting a cell that produces carotenoid in such an amount that is about 1.1 times to 1,000 times the production level of carotenoid produced by the cell prior to introduction of the DNA chain.

The DNA chain according to the present invention is a DNA chain described in (a), (b), (c), (d), (e) or (f), or a DNA chain that hybridizes therewith under a stringent condition.

The wordings "hybridize under a stringent condition" refers to the case where a probe hybridizes with a target sequence thereof but not with other nucleic acids in a complicated mixture of nucleic acids under a stringent condition. The stringent condition depends on the sequence, and differs depending on the environment. For a longer sequence, specific hybridization is achieved at higher temperature. In general, a highly stringent condition is selected such that it is lower by about 5 to 10° C. than the melting temperature of specific sequence at definite ion strength and pH. A low stringent condition is generally selected such that it is lower by about 15 to 30° C. than the melting temperature. The "melting temperature" is the temperature at which 50% of probes that are complementary to a target nucleic acid in equilibrium at definite ion strength, pH and nucleic acid. Any nucleic acids that do not hybridize with each other under a stringent condition are regarded as being substantially identical if the polypeptides coded by these nucleic acids are substantially identical. This occurs, for example, when copies of nucleic acid are generated by using the maximum codon degeneracy which is acceptable by genetic coding. In such a case, nucleic acids typically hybridize under a moderately stringent hybridization condition.

The wording "substantially identical" is used for sequences or partial sequences exhibiting at least 60%, preferably 80%, more preferably 90% or more nucleotide or amino acid residue identity when two nucleic acids or polypeptides are examined by using one of the later-described sequence comparing algorism or examined by manual alignment or visual check, and aligned to achieve the maximum correspondence in a comparison window. This definition also applies to such a sequence that a complement thereof hybridizes with a test sequence.

For sequence comparison, typically one sequence is prepared as a reference sequence, and a test sequence is compared with the reference sequence. When a sequence comparing algorism is used, a test sequence and a reference sequence are inputted to a computer, and partial coordinates are specified as is necessary, and a parameter of sequence algorism program is designated. Default values of the program may be used, or an alternative parameter may be designated. Then, the sequence comparing algorism calculates a percentage of sequence identity of the test sequence with respect to the reference sequence according to the parameter of the program. The method of sequence alignment for comparison is known in the art. An optimum sequence for comparison may be selected, for example, by local homology algorism described in Smith and Watreman, Adv. Appl. Math., 2:482 (1981), homology alignment algorism described in Needleman and Wunsch, J. Mol. Biol., 48:443 (1970), similarity inquiry method described in Person and Lipman, Proc. Natl. Acd. Sci. USA, 85:2444 (1988), and execution of these algorisms with a computer or execution by manual alignment and visual check.

PILEUP is one example of useful algorisms. PILEUP creates multiple sequences from related sequence group using a continuous pairwise alignment and gives relationship and percentage of sequence identity. PILEUP also plots tree or dendgram representing cluster relationship for use in making alignment. Another example of algorism suited for determining percentage of sequence identity and sequence similarity is BLAST algorism (Altschul et al., J. Mol. Biol., 215: 403-410 (1990)). In this algorism, the word lengths are fixed to 3 for protein and 11 for nucleic acid (3 for the case where the sequence is translated by a total of six reading frames). These lengths are the minimum values that are able to give high word scores to adequately significant ones, and are not too long to pass over short but significant patterns. BLAST algorism also conducts statistical analysis concerning similarity of two sequences.

The polypeptide encoded by the DNA chain of the present invention has an amino acid sequence of a sequence selected essentially from the group consisting of SEQ ID NO: 2, 3, 4, 5, 6 and 7. In the present invention, the polypeptide encoded by such a DNA chain may have some modifications such as deletion, substitution and addition at some of amino acids unless the carotenoid amount increasing activity as described above is impaired. This corresponds to the fact that "amino acid sequence has substantially a sequence selected essentially from the group consisting of SEQ ID NOs: 2, 3, 4, 5, 6 and 7". For example, those lacking the first amino acid (Met) of these enzymes are also included in the polypeptides or enzymes with modified amino acid sequence. DNA chains of the present invention encoding the respective polypeptides include not only those having base sequences encoding the amino acid sequences represented by SEQ ID NOs: 2, 3, 4, 5, 6 and 7 but also degenerate isomers which encode the same polypeptide but have different degenerate codons.

One means for acquiring a DNA chain having a base sequence encoding an amino acid sequence of the above protein is to chemically synthesize at least a part of the chain length according to a method of synthesizing nucleic acid synthesis, however, in consideration of multiplicity of the binding amino acids, it would be preferable to prepare a genomic DNA of *Paracoccus* sp. or the like, fragmenting into random fragments by restriction enzyme treatment using an appropriate restriction enzyme such as Sau3AI, preparing a library of *Escherichia coli* based on the cosmid method, and using a hybridization method with the use of an appropriate probe, rather than the chemical synthetic method. Furthermore, when an appropriate PCR primer can be manufactured, a desired DNA chain may be amplified by PCR method using the prepared genomic DNA as a template.

A DNA chain may be used without modification for transformation of an appropriate cell, however, it may be inserted into a plasmid vector before use. A plasmid vector can be genetically inserted into an appropriate position of a plasmid vector. The appropriate position may be selected so that regions concerning replication of plasmid vector, desired antibiotic marker and transmissivity are not broken.

In insertion to a plasmid vector, the above DNA chain may be genetically inserted without modification, however, a DNA chain having a promoter activity may be added. The term "promoter" used herein refers to a DNA sequence capable of controlling expression of a protein coding region or functional RNA, and as such, lac promoter, trc promoter and the like that function in *Escherichia coli* can be exemplified. In the case where the DNA chain is expressed in a marine bacterium, there is no limitation insofar as such DNA chain is a DNA chain including a promoter sequence functioning in cells. Preferably, the promoter is derived from marine bacteria. Preferably, by using a promoter of SEQ ID NO: 19, 20 or 21, it is possible to express an inserted gene encoding a carotenoid synthase. Alternatively, a part of polynucleotide of SEQ ID NO: 19, 20 or 21 may be used. A partial region can be identified by comparison of known promoter sequences. Furthermore, these sequences may have insertion or substitution of a base. Furthermore, mutations may be introduced at random and polynucleotides with improved promoter activity may be used. In general, a coding region of enzyme protein or the like is positioned on the 3' side of the promoter sequence. Commercially available plasmid vectors can be applicable if they already have a promoter sequence, and the promoter functions in a marine bacterium. Furthermore, the orientation in which a DNA chain is to be inserted may be any orientation insofar as the DNA chain functions.

As the plasmid vector, any vectors can be used insofar as they are present stable and replicable in transformed cells. Furthermore, as the plasmid vector, pUC series, pBR series and the like that are used for transformation of *Escherichia coli*, as well as shuttle vectors linked with a plasmid vector which is replicable in the objective cells can be exemplified. For the details, see published document (Barbara E. Funnell, PLASMID BIOLOGY, ASM press) In *Paracoccus* sp. of the present invention, a replicable plasmid vector is not particularly known. When there is no established host vector, a broad-host-range plasmid vector may be used. As such a vector, RK2, R751, RSF1010, R1162, pCU1, R46, pSA, R388, RA1 can be exemplified (Barbara E. Funnell, PLASMID BIOLOGY, ASM press). Furthermore, it may be inserted into an appropriate plasmid vector with the use of a replication region of a broad-host-range vector, and used as a shuttle vector. For example, a shuttle vector can be exemplified, which is prepared by inserting a replication region of RK2 vector into an appropriate position of a pUC series vector, and is able to utilize *Escherichia coli*. Also pBBR series plasmids can also be exemplified, which have relatively small DNA sizes and are replicable in a broad range of hosts. Examples of the pBBR series plasmids include pBBR122, pBBR1MCS, pBBR1MCS2, pBBR1MCS3, pBBR1MCS4, and pBBR1MCS5 (Non-patent document 5). These plasmid vectors are characterized, for example, by different antibiotic markers, and may be selected for use after evaluation of antibiotic resistance of a transformed cell. Furthermore, a plasmid retained by a cell to be transformed may be used.

By introducing a DNA chain of the present invention as described above, or a DNA chain inserted into an appropriate plasmid vector, into an appropriate carotenoid producing microorganism, it is possible to increase a carotenoid content. In the present invention, the following expression vectors are included: pBBR1MCS2CRT, pBBR1MCS2CRTrv, pBBR1MCS2CRTWZ, pBBR1MCS2CRTWZrv, pBBR1MCS2PcrtE1crtE, pBBR1MCS2PcrtE2crtE, pBBR1MCS2PcrtE1crtECRT, and combinations thereof. These vectors will be defined in Examples given later.

Preferred host cells can be broadly found in fungi and bacteria families, and are biological hosts that proliferate in wide ranges of temperature, pH and solvent resistance. For example, either of bacteria, yeast and filamentous fungi is a suitable host for expression of DNA chain of the present invention. Since mechanisms of transcription and translation of DNA chain, and biosynthesis mechanism of protein are common regardless of supply materials of cells, a functional gene will be expressed regardless of a carbon supply material used for culturing of culture. For large-scale culture of microorganism and functional gene expression, a wide variety of simple or complicated carbohydrates, organic acids and alcohols, and saturated hydrocarbons such as methane can be used, while photosynthetic or chemoautotrophic hosts can utilize carbon dioxide. However, a functional gene may be regulated, suppressed or lowered by a specific culture condition which may include forms and amounts of micronutrients including nitrogen, phosphorus, sulfur, oxygen, carbon or inorganic substances. Furthermore, regulation of functional gene may be achieved by a specific regulator substance which is added to a liquid culture and typically is not considered as a source of nutrient or energy.

Examples of the host include microorganism species such as *Aspergillus, Trichoderma, Pichia, Candida, Hansenula, Saccharomyces, Salmonella, Bacillus, Acinetobacter, Zymomonas, Agrobacterium, Erythrobacter, Chlorobium, Chromatium, Flavobacterium, Cytophaga, Rhodobacter, Rhocdococcus, Streptomyces, Brevibacterium, Corynebacteria, Mycobacterium, Deinococcus, Escherichia, Erwinia, Pantoea, Pseudomonas, Sphingomonas, Methylomonas, Methylobacter, Methylococcus, Methylosinus, Methylomicrobium, Methylocystis, Alcaligenes, Synechocystis, Synechococcus, Anabaena, Myxococcus, Thiobacillus, Methanobacterium, Paracoccus* and *Klebsiella*. Preferred are bacteria belonging to *Paracoccus*, which may be conveniently identified by those skilled in the art by taking a DNA sequence encoding 16S rRNA as an index. More preferred is *Paracoccus* sp. strain MBIC1143 for which carotenoid production amount is reported. A DNA base sequence encoding 16S rRNA of *Paracoccus* sp. strain MBIC1143 is disclosed to public. See, for example, Accession No. AB008114 of National Center for Biotechnology Information which is official database. A base sequence of DNA chain encoding 16S rRNA of *Paracoccus* sp. strain MBIC1143 is shown by SEQ ID NO: 24. Further preferred are strain TSN18E7 (see Japanese Patent Laid-Open Publication No. 2005-58216), and strain TSTT001 (see specification of Japanese Patent Application No. 2005-314667) which are mutants derived from *Paracoccus* sp. strain MBIC1143. It is, in particular, a mutant derivative strain which is free from regulation on various metabolic system concerning cell growth due to intracellular accumulation of carotenoids. In other words, it is a mutant strain for which regulation is cancelled by mutation treatment or the like. In cells, when a specific metabolic product accumulates, feedback inhibition or the like may occur by the metabolic product to stop subsequent synthesis of the metabolic product. The wording "canceling of regulation" means suspension of regulation mechanism in cells. There is an industrial successful case in lysine fermentation of amino acid. The mutation treatment may be carried out using a mutation treatment agent which is well-known in the art such as nitrosoguanidine, ethyl methane sulfonic acid, ultraviolet rays, radiation rays, or the like. The strain for which regulation is cancelled may be a natural mutant. Alternatively, mutants after mutation treatment and natural mutants may be isolated and obtained from a selective medium utilizing a metabolic analogue of carotenoids. The metabolic analogue is a substance that has a similar chemical structure to carotenoid, or a substance that shows a physiologic reaction similar to that of carotenoid in various intracellular reaction systems. Examples of the metabolic analog include β-ionone and α-ionone. Furthermore, a gene expression chip of host cell may be created, and an expression profile may be precisely analyzed under various culture conditions, and based on the gene expression profile under the environment where carotenoid accumulates in high density, a gene knockout or knock-in strain may be created and used.

The following is description of outline of a gene transduction procedure to a desired microorganism. A procedure or method for introduction and expression of an exogenous gene into a microorganism such as *Escherichia coli* includes those commonly used in the field of genetic engineering as well as those shown below in the present invention, and may be practiced according to such a procedure and method (for example, "Vectors for cloning genes", Method in Enzymology, 216, p. 469-631, 1992, Academic Press and, "Other bacterial systems", Method in Enzymology, 204, p. 305-636, 1991, Academic Press). Concrete examples include a heat-shock method, and an electroporation method.

As to a method of gene transduction into *Paracoccus* sp. in the present invention, no established technique is known. In such a case, as a method of introducing a gene in a mild condition, a conjugational transfer method using *Escherichia coli* is exemplified. The conjugational transfer method is a method in which a plasmid is introduced from a donor bacterium to a recipient bacterium by conjugation between these bacteria, and is advantageous in that the damage to the recipient bacterium is small. The conjugational transfer method using *Escherichia coli* is classified into two methods: a biparental transfer method and a triparental transfer method. In the former biparental transfer method, by co-culture of a plasmid donor bacterium which is *Escherichia coli* strain S17-1 incorporating in its chromosome a tra region which is responsible for self-transferability, with a recipient bacterium, it is possible to introduce the plasmid to the recipient bacterium from the donor bacterium by the action of tra (Non-patent document 6) Furthermore, when a plasmid vector (for example, the above pBBR1MCS) having a mob gene (Non-patent document 7) is used, it is possible to effectively introduce the plasmid into the recipient bacterium. The triparental transfer method is a method in which conjugation is caused by mixing *Escherichia coli* having a helper plasmid (for example, RK1), *Escherichia coli* having an appropriate plasmid vector and a bacterium to which a gene is to be introduced.

Both methods involve incubation on a filter for a certain time after mixing cells in a medium such as buffer at a certain temperature on a membrane disc. Regarding the conjugation condition for these cases, the temperature is usually, but not limited to, 20 to 30° C., and preferably 25° C. The incubation time is generally from several hours to several days. The mixing ratio of *Escherichia coli* and a bacterium to which a gene is to be introduced is not particularly limited. This is because when *Escherichia coli* or yeast to be conjugated is present even in a trace amount, a conjugant is obtained, and such a conjugant can be proliferated through isolation and culture. In order to achieve effective conjugation, the ratio of Escherichia coli and a bacterium to which a gene is to be introduced is, for example, 1:1 or 0.1:1.

After conjugational transfer, the conjugational-transferred cell may be isolated from other cells based on its characteristic acquired as a result of the conjugational transfer. For example, using an antibiotic resistance introduced into the used plasmid vector, only a conjugational-transferred cell into which the plasmid vector is introduced can be proliferated and isolated. All of these methods are well known by those skilled in the art. Furthermore, through combinational use of an antibiotic that prevents growth of Escherichia coli which is a donor of conjugational transfer, more efficient selection of conjugational-transferred cell is realized. Examples of the antibiotic include Carbenicillin, Ampicillin, Cefazollin, Piperacillin, Fosfomycin, Gentamicin, Streptomycin, Neomycin, Amikacin, Tetracyclin, Erythromycin, Lincomycin, Rifampicin, Nalidixic acid, and Novobiocin. Isolation of conjugational-transferred cell can be checked by plasmid extraction, PCR and the like techniques after culturing in an appropriate liquid culture.

By introduction and expression of a group of carotenoid synthesis gene according to the procedure or method of gene transduction to microorganism as described above, it is possible to obtain a microorganism capable of producing a great amount of carotenoid.

Using these transformants and an appropriate culture medium, it is possible to make various carotenoids accumulate in cells. For collection of carotenoids, carotenoid accumulating microorganism may be collected from the culture medium and extracted from an appropriate organic solvent. As an organic solvent, methanol, ethanol, isopropyl alcohol, acetone, methyl ethyl ketone, methyl isobutyl ketone, dichloromethane, chloroform, dimethylformamide, and dimethylsulfoxide are exemplified, with acetone being preferred. Furthermore, using a liquid chromatography, high purity separation is realized. As the isolation principle of the liquid chromatography, ion exchange, hydrophobic interaction, molecular sieve and the like can be exemplified. Reverse-phase chromatography and normal-phase chromatography are preferred.

The following examples are intended for concrete explanation of the present invention and not for limitation of the present invention. The gene recombinant experiments made herein are based on a standard method (Sambrook, J., Fritch, E. F., Maniatis, T., "Molecular cloning 3rd edition", Cold Spring Harbor Laboratory Press) unless otherwise specified.

Example 1

Preparation of Genomic DNA Derived from Paracoccus Strain MBIC1143 and Cloning of Carotenoid Synthesis Gene Paracoccus sp. strain MBIC1143 was cultured in an OEG culture medium (2 g/L of trypticase peptone, 1 g/L of yeast extract, 8.8 g/L of NaCl; 0.73 g/L magnesium sulfate heptahydrate, 3.6 g/L of anhydrous dipotassium phosphate, 1.4 g/L of potassium phosphate, 1 g/L of D-glucose) at 25° C. (rotary shaking at 120 rpm) for 3 days. Paracoccus sp. strain MBIC1143 was provided by Marin Biotechnology provided by Institute Co., Ltd.

A genomic DNA was prepared using a kit available from Gentra Systems, Inc. (Puregen Genomic DNA isolation kit) (about 50 ng/ml) Using the prepared DNA as a template, a carotenoid synthesis gene was amplified by PCR. Base sequences of genes (crtW, crtZ, crtY, crtI, crtB, crtE) constituting a group of carotenoid synthesis genes of Paracoccus sp. strain MBIC1143 are described in Non-patent document 2 and Patent document 3. Referring to these published data, we created a base sequence containing the above genes. SEQ ID NO: 1 shows a sequence of 7,029 bases. FIG. 1 shows a structure of gene cluster. PCR primers (SEQ ID NO: 13: 5'-gcggatccggcgaccttgcggcgctg-3') and SEQ ID NO: 14: 5'-cgggatcctgtcgcggtccctgggg-3') were created with reference to Non-patent document 2. PCR was conducted in the following manner. To 1.0 µL of prepared DNA, 13.5 µL of water, and 25 µL 2×High GC buffer (TAKARA BIO INC.) were added, and heated for 10 minutes at 94° C. After cooling on ice, 8 µL of dNTP, 1.0 µL of 10 pmol/µL forward primer represented by SEQ ID NO: 8, and 1.0 µL of 10 pmol/µL reverse primer represented by SEQ ID NO: 9 were added, and finally 0.5 µL of exTaqDNA polymerase (TAKARA BIO INC.) was added. The reaction included 30 cycles (each cycle consists of a step of 30 sec. at 94° C., a second step of 30 sec. at 60° C. and a third step of 4 min. at 72° C.), followed by reaction for 10 minutes at 72° C. The resultant PCR product was treated with phenol/chloroform, and then subjected to 0.9% agarose electrophoresis to extract and purify an objective product (about 5.4 k base) (QIAgen Gel Extraction Kit available from QIAGEN). The base sequence is shown by SEQ ID NO: 8. The purified DNA (to which a restrictive site of enzyme BamHI is inserted by PCR primer) was treated with a restriction enzyme BamHI, and purified by phenol/chloroform and ethanol precipitation. Then the DNA treated with the restriction enzyme was ligated to the BamHI site of the pUC19 plasmid vector (TAKARA BIO INC.) and after gene transduction by a heat shock method, Escherichia coli strain JM109 was transformed in a LB (Luria-Bertani) agar culture medium containing 100 µg/ml of carbenicillin.

An arbitrary transformant was cultured in a LB culture medium (37° C., 18 hours), and plasmid was extracted using a plasmid extraction kit (available from QIAGEN). Treatment of plasmid with a restriction enzyme BamHI demonstrated the presence of the intended insert. The plasmid vector where a carotenoid synthesis gene from Paracoccus was cloned was named pUCCRT. The structure of the prepared plasmid is shown in FIG. 3. According a method of Japanese patent application No. 2005-106045 as recited above, pUCCRT was checked for exhibition of carotenoid synthesis activity in Escherichia coli.

Example 2

Preparation of Paracoccus Expression Vector

Plasmid vector pUCCRT was treated with a restriction enzyme BamHI, and a carotenoid synthesis gene fragment (about 5.4 k base) was obtained. Then the fragment was inserted into BamHI site in a broad-host-range vector pBBR1MCS2. Gene transduction into Escherichia coli strain JM109 was conducted by a heat shock method, and then transformation in a LB agar culture medium containing 50 µg/ml of kanamycin was conducted. An arbitrary transformant having acquired kanamycin resistance was cultured in a LB culture medium (37° C., 18 hours), and plasmid was extracted using a plasmid extraction kit (available from QIAGEN). Treatment of plasmid with a restriction enzyme BamHI demonstrated the presence of the intended insert. There are two orientations for insertion of the insert fragment. To be more specific, a vector in which transcription directions of lac promoter and insert fragment in the pBBR1MCS2 vector are the same (pBBR1MCS2CRT) and a vector in which transcription directions of lac promoter and insert fragment in the pBBR1MCS2 vector are opposite (pBBR1MCS2CRTrv). Structures of prepared vectors are shown in FIG. 4.

Example 3

Homogeneous Expression of Carotenoid Synthesis Gene in *Paracoccus* Bacteria

Each of the vectors pBBR1MCS2CRT and pBBR1MCS2CRTrv into which a carotenoid synthesis gene fragment was cloned was introduced into *Escherichia coli* strain S17-1 by a heat shock method, and transformation was effected in a LB agar culture medium containing 50 μg/ml of kanamycin and 10 μg/ml of streptomycin. An arbitrary transformant having acquired kanamycin resistance was cultured in a LB culture medium (37° C., 18 hours), and a plasmid was extracted using a plasmid extraction kit (available from QIAGEN) to check whether an objective plasmid was introduced. Then by treatment with a restriction enzyme BamHI, whether the plasmid was properly replicated in *Escherichia coli* strain S17-1 was checked. The two different plasmid vectors were respectively replicated without occurrence of recombination in *Escherichia coli* strain S17-1.

*Escherichia coli* strain S17-1 having the pBBR1MCS2CRT plasmid vector into which a carotenoid synthesis gene is inserted was cultured in a LB culture medium containing 50 μg/ml of kanamycin and 10 μg/ml of streptomycin (37° C.), and a liquid culture containing cells in logarithmic growth phase was obtained. Turbidity (OD 660 nm) was measured, and the culture was diluted in the same culture medium so that the turbidity was 0.1. In parallel with this, *Paracoccus* bacterium was cultured in an OEG culture medium of Example 1 (25° C.), and a liquid culture containing cells in logarithmic growth phase was obtained. In the same manner as described above, turbidity was measured and the culture was diluted in an OEG culture medium so that the turbidity was 1.0. Each 1.0 mL of these solutions was put into 5 mL-capacity syringe, and the solution in the syringe was passed through a membrane attached to a membrane holder (available from Advantec) to collect cells. After collection of cells, the membrane was removed from the holder, and placed on an OEG agar culture medium (the cells upside), and culturing for causing conjugational transfer was conducted (25° C., 4 hours). After culturing, the membrane was put into 1.0 ml of an OEG culture medium, and conjugational-transferred cells were removed from the membrane filter by agitation. The solution was then diluted in an OEG culture medium to an appropriate concentration, and spread on an OEG agar medium containing 50 μg/ml of kanamycin and 15 μg/ml of amikacin (available from Sigma) and cultured at 25° C. The amikacin was added so as to suppress of growth *Escherichia coli*.

A colony appearing at 3 days of culturing was picked up, and cultured in an OEG culture medium containing 50 μg/ml of kanamycin (25° C.) to extract a plasmid. Plasmid extraction was carried out with the use of a plasmid extraction kit available from QIAGEN as is the case with the *Escherichia coli* strain JM109. Electrophoresis in 0.9% agarose of the resultant liquid extract resulted in the same result as that of pBBR1MCS2CRT carried in *Escherichia coli* strain S17-1. This demonstrated that plasmid transfer from *Escherichia coli* to *Paracoccus* bacterium proceeded successfully. The same examination was conducted for pBBR1MCS2CRTrv.

Example 4

Quantification of Astaxanthin Production in Transformed *Paracoccus* Bacterium

*Paracoccus* bacteria having either of plasmids pBBR1MCS2CRT and pBBR1MCS2CRTrv were respectively cultured in an OEG culture medium containing 100 μg/ml of kanamycin (25° C.). Culture was executed in 60 mL of culture medium put into a 100 mL-capacity Erlenmeyer flask equipped with a baffle placed on a rotary shaking incubator rotating at 120 rpm.

Sampling was made at an appropriate point of time, and after cell collection by centrifugal operation, carotenoids was extracted from acetone and quantified. Quantity of carotenoids was measured by high performance liquid chromatography (HPLC) using a reverse-phase column, and conducted in the following operation procedure. To be more specific, a part of liquid culture was centrifuged to collect cells, and the cells were added with an appropriate amount of pure water and suspended for 10 minutes by a tube mixer. Then 9 times amount of acetone to pure water was added and stirred for 30 minutes by a tube mixer. After that, centrifugation at 14,000 rpm for 5 minutes was conducted, and the supernatant was subjected to quantification by HPLC. As the HPLC column, TSKgel ODS-80 (available from TOSOH Corporation) was used, and measurement was conducted at flow rate of 1.0 ml/min and detection wavelength of 470 nm. Using standard astaxanthin (available from Sigma), a calibration curve was prepared, and a production amount of astaxanthin in the culture was calculated. As a control of plasmid introduced strains, a strain having only pBBR1MCS2 vector to which no carotenoid synthesis gene is inserted was also prepared. As shown in Table 1, significant increase in production amount of astaxanthin was observed in the *Paracoccus* bacteria having a carotenoid synthesis gene.

Furthermore, a wild type strain of *Paracoccus* sp., strain MBIC1143 was subjected to mutagenesis, and gene transduction into strain TSN18E7 with improved astaxanthin synthesis amount was conducted in a similar manner by conjugational transfer. As is the case with the strain MBIC1143, significant increase in production amount of astaxanthin was observed (Table 1).

In the gene-transduced mutant strain TSN18E7, in particular, the increase is significant at 72 hours of culture. The ability to synthesize astaxanthin which is the final product of carotenoid synthesis in short time demonstrates the effect of plasmid vector that is prepared by insertion of a carotenoid synthesis gene. *Paracoccus* sp. strain TSN18E7 is deposited to International Patent Organism Depositary, National Institute of Advanced Industrial Science and Technology under the number of FERM P-19746.

TABLE 1

Production amount of astaxanthin by gene transduced *Paracoccus* bacterium

| Strain | Introduced plasmid | Production amount of astaxanthin (mg/L) | |
|---|---|---|---|
| | | 72-hour culture | 144-hour culture |
| Wild-type | pBBR1MCS2 | 2.0 | 1.7 |
| | pBBR1MCS2CRT | 3.6 | 3.0 |
| | pBBR1MCS2CRTrv | 3.8 | 2.9 |
| Mutant TSN18E7 | pBBR1MCS2 | 5.1 | 20.5 |
| | pBBR1MCS2CRT | 30.0 | 28.1 |
| | pBBR1MCS2CRTrv | 30.0 | 28.3 |

Example 5

Analysis of Promoter Sequence of Inserted Carotenoid Synthesis Gene

Similarly to Example 4, a carotenoid synthesis gene fragment was inserted into vector pBBR1MCS2, and homogenously expressed in a *Paracoccus* bacterium. Significant increase in production amount of astaxanthin which is one kind of carotenoids was observed. In addition, improvement in activity was observed regardless of the orientation of insertion into a vector. This suggests that the carotenoid synthesis gene is expressed without using the function of lac promoter inserted into the vector pBBR1MCS2. In view of this, we made promoter analysis for a sequence located on upstream side in the transcription direction of the amplified carotenoid synthesis gene (from 1 to 450 described in SEQ ID NO: 1). For analysis, commercially available software GENETYX (available from GENETICS) was used. As a result of analysis, a sequence functioning as a promoter was found on upstream side of crtW gene in the amplified DNA (Table 2). The base sequence from the first position to just proximal to crtW gene in SEQ ID NO: 19 can be estimated as a base sequence having a promoter activity in *Paracoccus* sp. The promoter score value in Table is a value calculated by the GENETYX software, and it can be interpreted that the higher the value the more likely the promoter activity be present.

TABLE 2

| Analyzed promoter sequence | | |
|---|---|---|
| | Promoter sequence | |
| Promoter score | −35 region | −10 region |
| 44.97 | TGGAAA | TAGTCT |
| 31.95 | ATGGAA | TAGTCT |

Example 6

Preparation of β-Carotene Oxidase Expression Vector

Genomic DNA of *Paracoccus* sp. was prepared in a similar manner as described in Example 1. Then, a region containing crtW and crtZ which are genes of β-carotene oxidase was amplified by PCR. The base sequence is shown in SEQ ID NO: 9. For PCR, primers of SEQ ID NO: 13 and SEQ ID NO: 15('5-cgggatccgcagggcgatcagcccgttggcaagg-3') were used. Then, to 1.0 μL of the prepared DNA serving as a template, 16.5 μL of water, and 25 μL of 2×High GC buffer (TAKARA BIO INC.) were added and heated for 10 minutes at 94° C. After cooling on ice, 5 μL of dNTP, 2.0 μL of 10 pmol/μL forward primer represented by SEQ ID NO: 13, 2.0 μL of 10 pmol/μL reverse primer represented by SEQ ID NO: 15, and finally 0.5 μL of exTaq DNA polymerase (TAKARA BIO INC.) were added. The reaction included 30 cycles (each cycle consists of a step of 30 sec. at 94° C., a second step of 30 sec. at 60° C. and a third step of 2 min. at 72° C.), followed by reaction for 7 minutes at 72° C. The amplified fragment was examined by agarose electrophoresis and extracted and purified (QIAgen Gel Extraction Kit available from QIAGEN). For allowing insertion into BamHI site of plasmid vector pBBR1MCS2, the purified DNA was digested with a restriction enzyme BamHI. After ligation, gene transduction into *Escherichia coli* strain JM109 was effected by a heat shock method, followed by transformation in a LB agar culture medium containing 50 μg/ml of kanamycin. An arbitrary transformant having acquired kanamycin resistance was cultured in a LB culture medium (37° C., 18 hours), and plasmid was extracted using a plasmid extraction kit (available from QIAGEN). Treatment of plasmid with a restriction enzyme BamHI demonstrated the presence of the intended insert. There are two orientations for insertion of the insert fragment. To be more specific, a vector in which transcription directions of lac promoter and insert fragment in the pBBR1MCS2 vector are the same (pBBR1MCS2CRTWZ) and a vector in which transcription directions of lac promoter and insert fragment in the pBBR1MCS2 vector are opposite (pBBR1MCS2CRTWZrv). Structures of the prepared vectors are shown in FIG. 5.

Example 7

Expression of β-Carotene Oxidizing Enzyme Expression Vector in *Paracoccus* sp.

Likewise the above Example 3, each of pBBR1MCS2CRTWZ and pBBR1MCS2CRTWZrv was introduced into *Escherichia coli* strain S17-1, and a mutant of *Paracoccus* sp. was transformed by conjugational transfer. After culturing for 3 days, carotenoid was quantified by HPLC. The result is shown in Table 3. In this table, "Ax" represents astaxanthin, and "TC" represents total carotenoid.

TABLE 3

| Production amount of carotenoid by gene transduced *Paracoccus* bacterium | | | | |
|---|---|---|---|---|
| Strain | Introduced construct | OD660 nm | Ax (mg/L) | TC (mg/L) |
| TSN18E7 | pBBR1MCS2 | 4.3 | 6.1 | 29.0 |
| | pBBR1MCS2CRTWZ | 4.1 | 22.4 | 27.0 |
| | pBBR1MCS2CRTWZrv | 3.8 | 19.3 | 25.0 |

As shown in Table 3, synthesis of astaxanthin was significantly increased due to the effect of introduced gene construct, namely increase in expression amount of β-carotene oxidizing enzyme while no increasing effect for total carotenoid was observed.

Example 8

Preparation of Geranylgeranyl Diphosphate Synthesis Gene Expression Vector

Genomic DNA of *Paracoccus* sp. was prepared in a similar manner to Example 1. Then geranylgeranyl diphosphate synthase gene (crtE) region was amplified by PCR. Since a promoter region which is expected to be present on upstream side of the crtE gene is unknown, referring to the base sequence of SEQ ID NO: 1, we designed and used two sets of PCR primers having different hybridizing regions: a set of primers represented by SEQ ID NO: 16 (5'-ctagtctagatgcttgacaatccgggt-gacgcgg-3') and SEQ ID NO: 17 (5'-tgggagctcatcacgcctag-gcgcgcgcggcgtag-3') and a set of primers represented by SEQ ID NO: 18 (5'-ctagtctagagccggtccactgaccttgttggac-3') and SEQ ID NO: 17. The former set amplifies a region of about 1.2 k base, and the latter set amplifies a region of 1.1 k base. The respective base sequences are shown by SEQ ID NO: 10 and SEQ ID NO: 11. The longer amplified region was named PcrtE1crtE, and the shorter amplified region was named PcrtE2crtE. As to PcrtE1crtE, first, 1.0 μL of prepared DNA which serves as a template of PCR was added with 16.5 μL of water, and 25 μL of 2×High GC buffer (TAKARA BIO INC.), and heated for 10 minutes at 94° C. After cooling on ice, 5 μL of dNTP, 2.0 μL of 10 pmol/μL forward primer represented by SEQ ID NO: 16, 2.0 μL of 10 pmol/μL reverse primer represented by SEQ ID NO: 17, and finally 0.5 μL of exTaq DNA polymerase (TAKARA BIO INC.) were added. The reaction included 30 cycles (each cycle consists of a step of 30 sec. at 94° C., a second step of 30 sec. at 60° C. and a third step of 2 min. at 72° C.), followed by reaction for 7 minutes at 72° C. The amplified fragment was examined by agarose electrophoresis and extracted and purified (QIAgen Gel Extraction Kit available from QIAGEN). Furthermore, terminals for insertion into a plasmid vector were arranged by digestion with restriction enzymes Xba I and SacI. In a similar manner, PcrtE2 was prepared using primers described in SEQ ID NO: 17 and SEQ ID NO: 18.

Next, pBBR1MCS2 which is a plasmid vector into which an insert is to be inserted was digested with restriction enzymes BtsI and Bsu36I to cause unneeded DNA chains drop out. Following extraction from phenol/chloroform, ethanol precipitation was conducted for purification. Furthermore, single-stranded oligonucleotides described in SEQ ID NOs: 22 (5'-tcatctagaggtaccatatgaagcttgagctcct-3') and 23 (5'-gagctcaagcttcatatggtacctctaga-3') were caused to anneal, and the resultant duplex was ligated to the purified DNA fragment. This duplex was designed to include restriction sites of restriction enzymes SacI and XbaI. After ligation, *Escherichia coli* JM109 was transformed in a LB agar culture medium containing 50 μg/ml of kanamycin, to obtain a vector into which the duplex was inserted. This was named pBBR1MCS2oligo.

Then pBBR1MCS2oligo was digested with restriction enzymes SacI and XbaI to arrange terminals for insertion of the insert. After ligation, *Escherichia coli* JM109 was transformed in a LB agar culture medium containing 50 μg/ml of kanamycin. An arbitrary colony was picked up and cultured, and a plasmid was prepared. The plasmid was subjected to electrophoresis to confirm that it was an intended construct. The construct having an insert of longer region was named pBBR1MCS2PcrtE1crtE, and the construct having an insert of shorter region was named pBBR1MCS2PcrtE2crtE. The respective structures are shown in FIG. 6.

Example 9

Expression of Geranylgeranyl Diphosphate Synthase in *Paracoccus* sp. Bacterium

Likewise the above Example 3, each of pBBR1MCS2PcrtE1crtE and pBBR1MCS2PcrtE2crtE was introduced into *Escherichia coli* strain S17-1, and a mutant of *Paracoccus* sp. was transformed by conjugational transfer. After culturing for 5 days likewise Example 4, carotenoid was quantified. The result is shown in Table 4.

TABLE 4

Production amount of carotenoid by gene transduced *Paracoccus* bacterium

| Strain | Introduced construct | OD660 nm | Carotenoid (mg/L) |
|---|---|---|---|
| TSN18E7 | — | 6.2 | 34.2 |
|  | pBBR1MCS2PcrtE1crtE | 1.0 | Trace amount |
|  | pBBR1MCS2PcrtE2crtE | 1.1 | Trace amount |
| TSTT001 | — | 11 | 30.0 |
|  | pBBR1MCS2PcrtE1crtE | 6.6 | 44.4 |
|  | pBBR1MCS2PcrtE2crtE | 7.2 | 43.0 |

As shown in Table 4, in the mutants TSN18E7 into which these gene constructs were introduced, bacteriolysis was observed, and increase in carotenoid synthesis amount was not observed. On the other hand, in the mutant TSTT001 with improved growth ability, a supply amount of geranylgeranyl diphosphate which is a product was increased by the effect of these constructs, namely increased amount of expression of geranylgeranyl diphosphate synthase, and a carotenoid synthesis amount was increased by the series of carotenoid synthases encoded by chromosome of *Paracoccus*. The mutant strain TSTT001 is deposited to International Patent Organism Depositary, National Institute of Advanced Industrial Science and Technology under the number of FERM P-20670.

Example 10

Promoter Sequence on Upstream Side of Geranylgeranyl Diphosphate Synthesis Gene

As described in Example 7, it was found that carotenoid synthesis amount was significantly increased when an upstream sequence is added to the region of 882 base encoding geranylgeranyl diphosphate synthase. In other words, it was found that a base sequence of about 300 bases or about 200 bases located on upstream side of ORF of geranylgeranyl diphosphate synthase is a DNA chain having a promoter activity. These base sequences are described in SEQ ID NO: 20 and SEQ ID NO: 21.

Example 11

Preparation of Plasmid Vector Combining Geranylgeranyl Diphosphate Synthesis Gene and Carotenoid Synthesis Gene The plasmid pBBR1MCS2PcrtE1crtE described in Example 7 was digested with a restriction enzyme XbaI. The cut terminal was blunted with a DNA Blunting Kit (TAKARA BIO INC.), and phenol/chloroform extraction, and purification by ethanol precipitation were carried out. Then, the carotenoid synthesis gene fragment that was prepared in Example 2 and digested with a restriction enzyme BamHI was similarly blunted, followed by phenol/chloroform extraction and purification by ethanol precipitation. These are then ligated, and *Escherichia coli* JM109 was transformed in a LB agar culture medium containing 50 μg/ml of kanamycin. An arbitrary colony was picked up and cultured, and a plasmid was prepared. The plasmid was subjected to electrophoresis to confirm that it was an intended construct. The base sequence of the prepared insert fragment is shown in SEQ ID NO: 12. This construct was named pBBR1MCS2PcrtE1crtECRT. FIG. 7 shows the structure thereof.

Example 12

Expression of Plasmid Vector Combining Geranylgeranyl Diphosphate Synthesis Gene and Carotenoid Synthesis Gene Likewise the above Example 3, pBBR1MCS2PcrtE1crtECRT was introduced into *Escheri-* chia coli strain S17-1, and a mutant of *Paracoccus* sp. was transformed by conjugational transfer. Likewise Example 4, carotenoid was quantified by HPLC after culturing for 5 days. The result of quantification is shown in Table 5. In this table, "Ax" represents astaxanthin, and "TC" represents total carotenoid. FIG. 8 shows a HPLC pattern of strain TSTT001 at 3 days of culture.

TABLE 5

Production amount of carotenoid by gene transduced *Paracoccus* bacterium

| Strain | Introduced construct | OD660 nm | Ax (mg/L) | TC (mg/L) |
|---|---|---|---|---|
| TSN18E7 | — | 6.1 | 20.3 | 33.2 |
|  | pBBR1MCS2PcrtE1crtECRT | 5.3 | 30.5 | 42.2 |
| TSTT001 | — | 10.5 | 17.8 | 31.1 |
|  | pBBR1MCS2PcrtE1crtECRT | 7.4 | 33.7 | 56.5 |

As shown in Table 5, the production amounts of astaxanthin and carotenoid significantly increased owing to the construct pBBR1MCS2PcrtE1crtECRT. That is, due to the expression of geranylgeranyl diphosphate synthase, geranylgeranyl diphosphate which is a synthesis material of carotenoid is synthesized at high density, and then a series of carotenoid synthases are excessively expressed due to the transduced construct to lead efficient synthesis of astaxanthin. As can be seen from FIG. 8, at 3 days of culture, the synthesis amount of astaxanthin was significantly increased due to pBBR1MCS2PcrtE1crtECRT which is a gene introduced into the strain TSTT001.

INDUSTRIAL APPLICABILITY

In the present invention, we revealed the function of gene or gene group that increases carotenoid production amount, and succeeded in improving natural microorganisms having carotenoid productivity. Therefore, by using the microorganisms improved by the present invention, it is possible to dramatically increase the productivity of carotenoids which are useful as feed or food.

SEQUENCE LISTING

Figure 1:
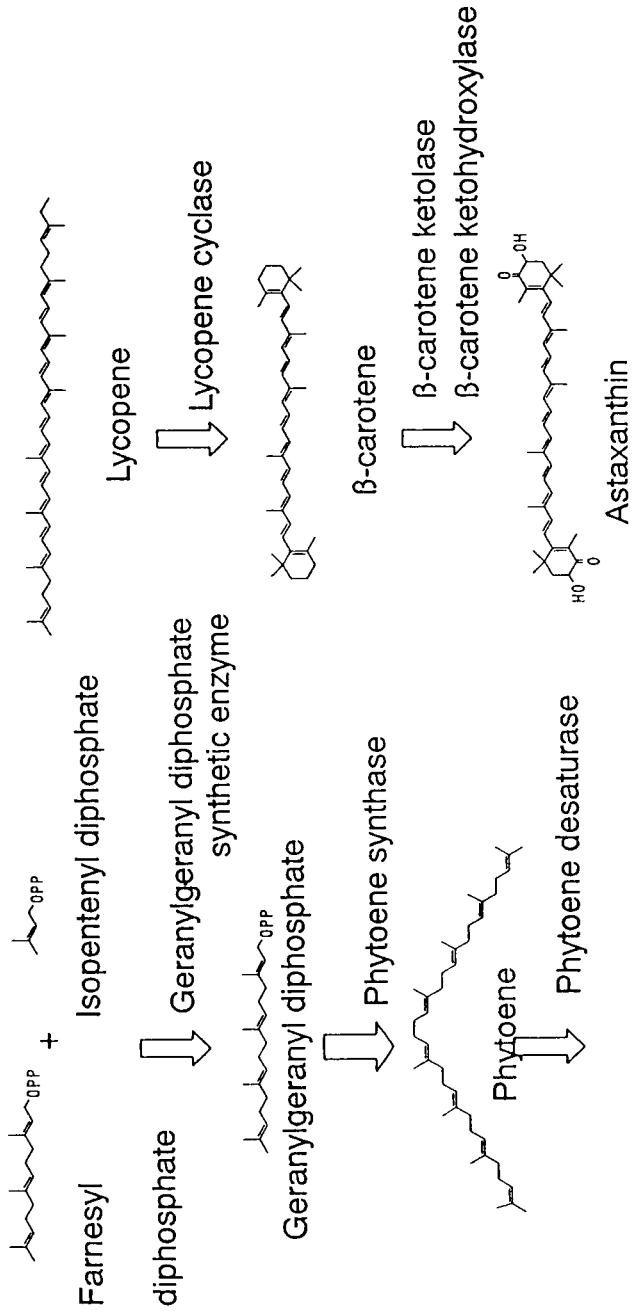
FIG. 1 A chart of carotenoid biosynthesis pathway.
Figure 2:
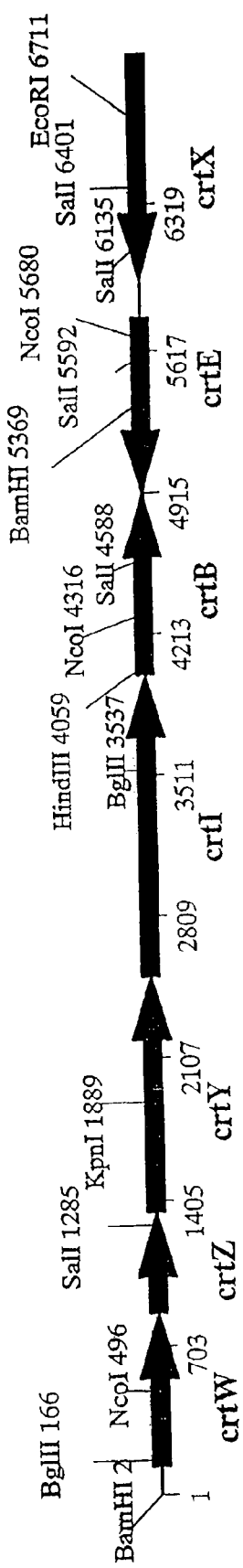
FIG. 2 A view showing a carotenoid synthesis gene.
Figure 3:
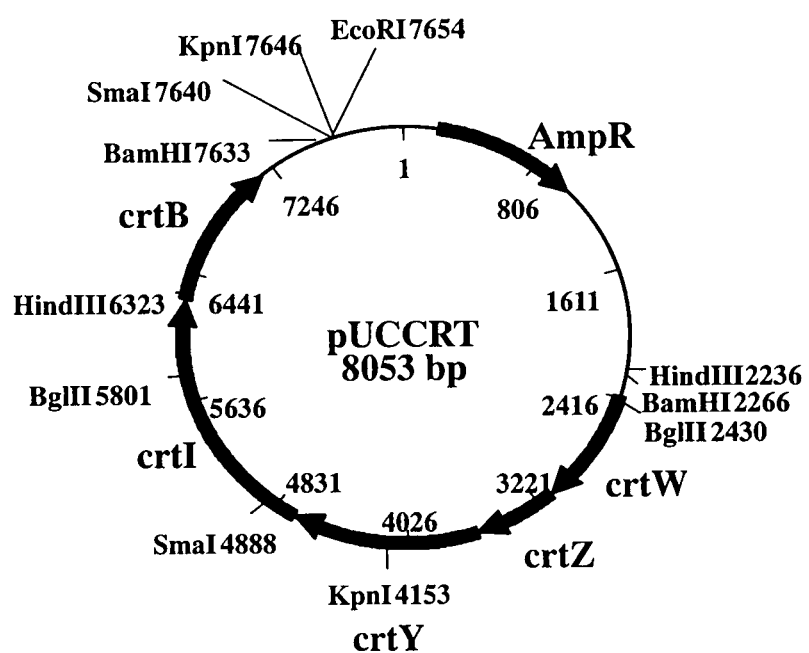
FIG. 3 A view showing a structure of plasmid vector pUC-CRT.
Figure 4:
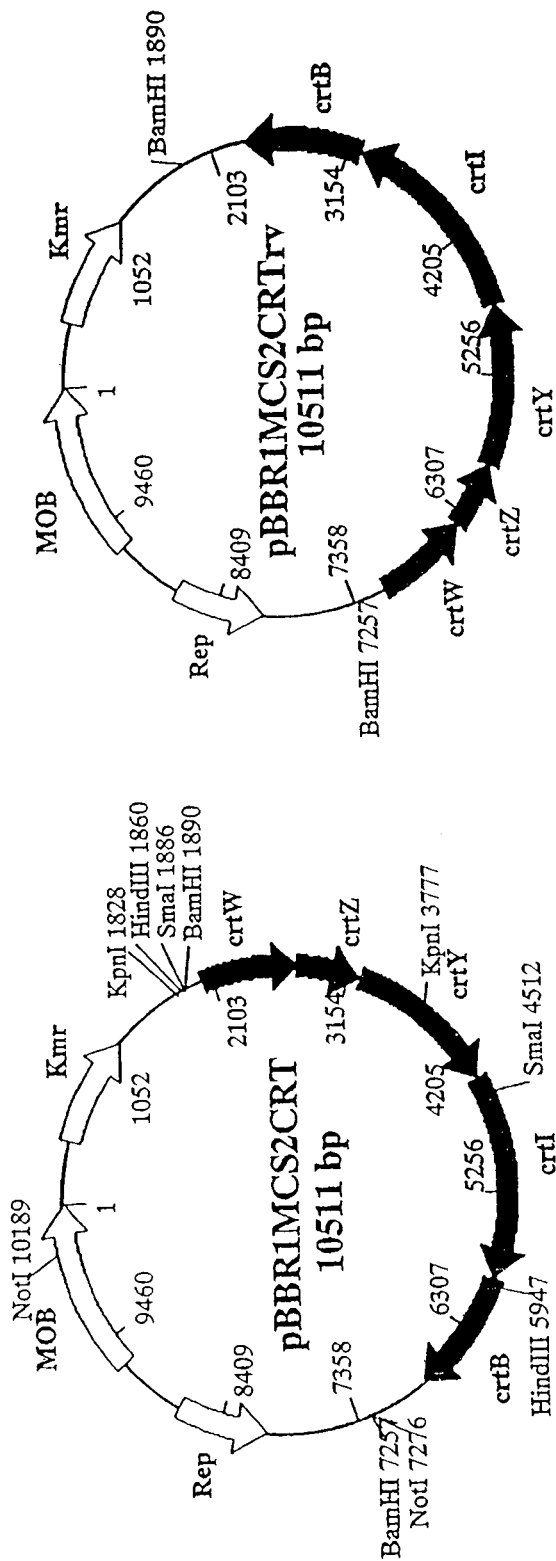
FIG. 4 A view showing structures of plasmid vectors pBBR1MCS2CRT and pBBR1MCS2CRTrv.
Figure 5:
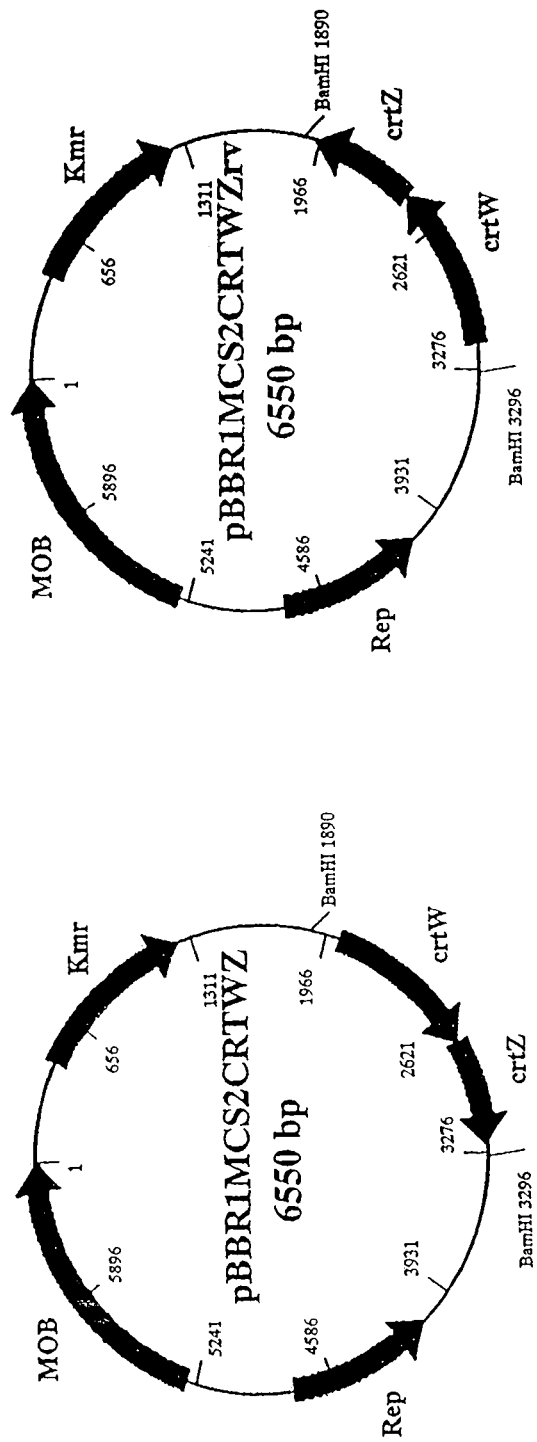
FIG. 5 A view showing structures of plasmid vectors pBBR1MCS2CRTWZ and pBBR1MCS2CRTWZrv.
Figure 6:
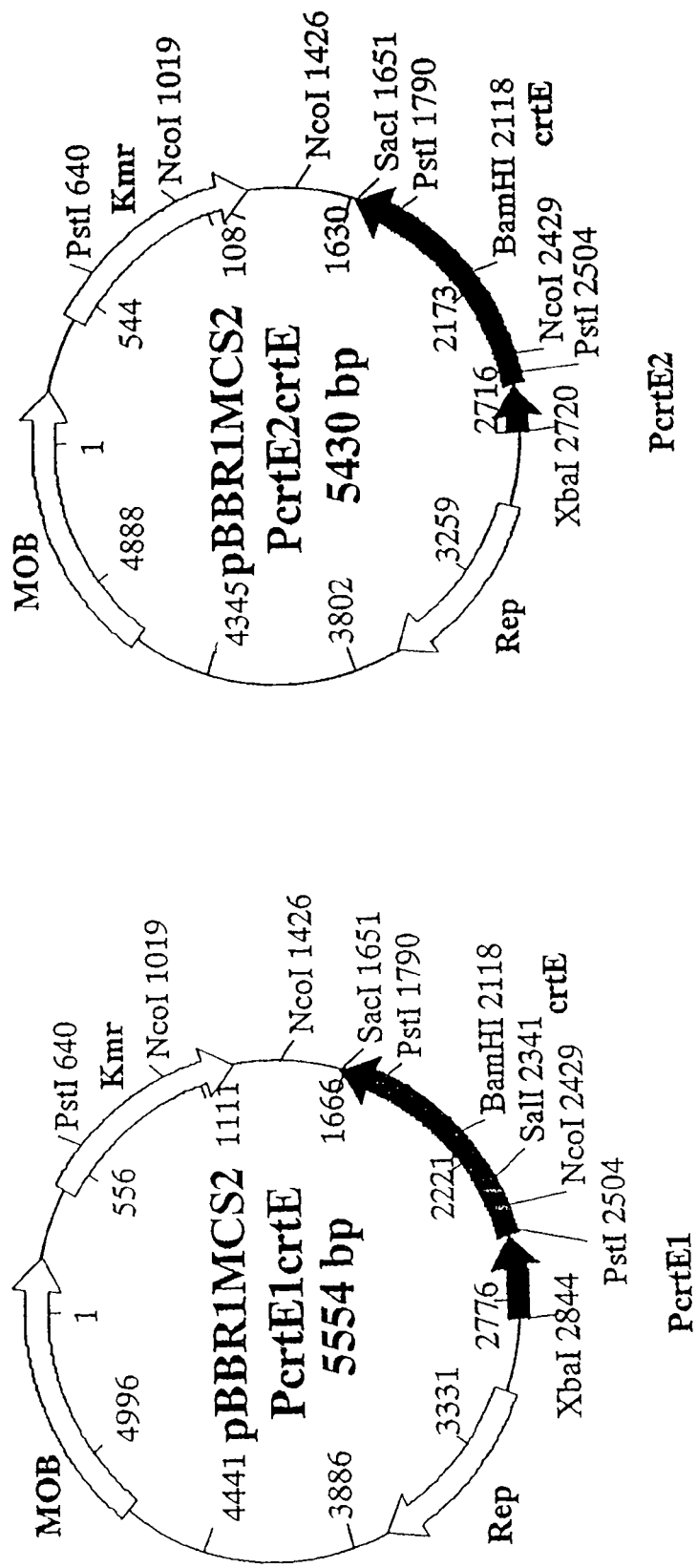
FIG. 6 A view showing structures of plasmid vectors pBBR1MCS2PcrtE1crtE and pBBR1MCS2PcrtE2crtE.
Figure 7:
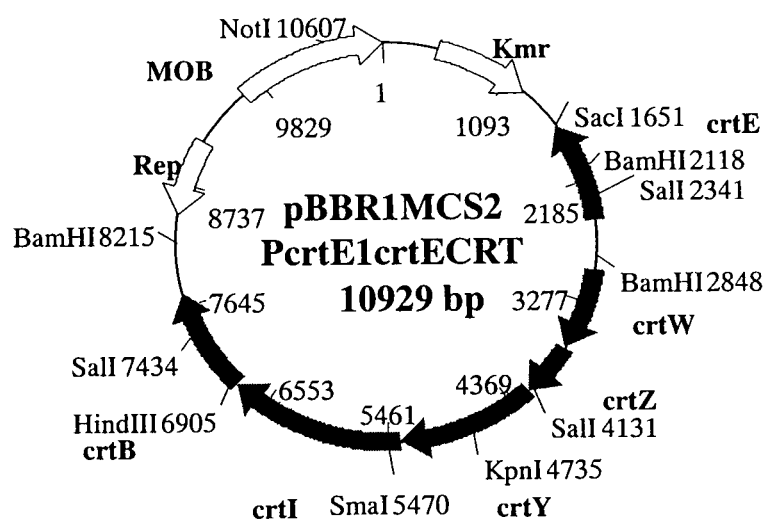
FIG. 7 A view showing structures of a plasmid vector pBBR1MCS2PcrtE1crtECRT.
Figure 8:
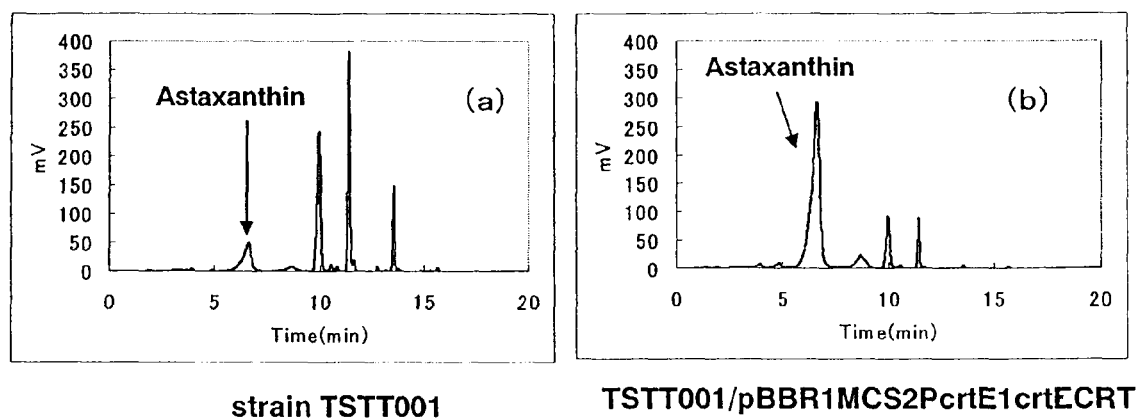
FIG. 8 A view illustrating the effect of increasing carotenoid synthesis amount of a bacterium recombined by the plasmid vector pBBR1MCS2PcrtE1crtECRT.

```
<160> NUMBER OF SEQ ID NOS: 24

<210> SEQ ID NO 1
<211> LENGTH: 7029
<212> TYPE: DNA
<213> ORGANISM: Paracoccus sp.
<220> FEATURE:
<221> NAME/KEY: modified_base
<222> LOCATION: (7024)..(7024)
<223> OTHER INFORMATION: a, t, g or c

<400> SEQUENCE: 1
ggatccggcg accttgcggc gctgcgccgc gcgcctttgc tggtgcctgg gccgggtggc      60
caatggtcgc aagcaacggg gatggaaacc ggcgatgcgg gactgtagtc tgcgcggatc     120
gccggtccgg gggacaagat gagcgcacat gccctgccca aggcagatct gaccgccacc     180
agcctgatcg tctcgggcgg catcatcgcc gcttggctgg ccctgcatgt gcatgcgctg     240
tggtttctgg acgcagcggc gcatcccatc ctggcgatcg caaatttcct ggggctgacc     300
tggctgtcgg tcggattgtt catcatcgcg catgacgcga tgcacgggtc ggtggtgccg     360
gggcgtccgc gcgccaatgc ggcgatgggc cagcttgtcc tgtggctgta tgccggattt     420
tcgtggcgca agatgatcgt caagcacatg gcccatcacc gccatgccgg aaccgacgac     480
gaccccgatt tcgaccatgg cggcccggtc cgctggtacg cccgcttcat cggcacctat     540
ttcggctggc gcgagggggct gctgctgccc gtcatcgtga cggtctatgc gctgatcctt     600
ggggatcgct ggatgtacgt ggtcttctgg ccgctgccgt cgatcctggc gtcgatccag     660
ctgttcgtgt tcggcacctg gctgccgcac gcccccggcc acgacgcgtt cccggaccgc     720
cacaatgcgc ggtcgtcgcg gatcagcgac cccgtgtcgc tgctgacctg ctttcacttt     780
ggcggttatc atcacgaaca ccacctgcac ccgacggtgc cgtggtggcg cctgcccagc     840
```

```
acccgcacca agggggacac cgcatgacca atttcctgat cgtcgtcgcc accgtgctgg      900
tgatggagtt gacggcctat tccgtccacc gctggatcat gcacgccccc ctgggctggg      960
gctggcacaa gtcccaccac gaggaacacg accacgcgct ggaaaagaac gacctgtacg     1020
gcctggtctt tgcggtgatc gccacggtgc tgttcacggt gggctggatc tgggcgccgg     1080
tcctgtggtg gatcgccttg ggcatgactg tctatgggct gatctatttc gtcctgcatg     1140
acgggctggt gcatcagcgc tggccgttcc gttatatccc gcgcaagggc tatgccagac     1200
gcctgtatca ggcccaccgc ctgcaccatg cggtcgaggg gcgcgaccat tgcgtcagct     1260
tcggcttcat ctatgcgccc ccggtcgaca agctgaagca ggacctgaag atgtcgggcg     1320
tgctgcgggc cgaggcgcag gagcgcacgt gacccatgac gtgctgctgg caggggcggg     1380
ccttgccaac gggctgatcg ccctggcgct gcgcgcggcg cggcccgacc tgcgcgtgct     1440
gctgctggac catgccgcag gaccgtcaga cggccacacc tggtcctgcc acgaccccga     1500
cctgtcgccg gactggctgg cgcggctgaa gcccctgcgc cgcgccaact ggcccgacca     1560
ggaggtgcgc tttccccgcc atgcccggcg gctggccacc ggttacgggt cgctggacgg     1620
ggcggcgctg gcggatgcgg tggtccggtc gggcgccgag atccgctggg acagcgacat     1680
cgccctgctg gatgcgcagg gggcgacgct gtcctgcggc acccggatcg aggcgggcgc     1740
ggtcctggac gggcggggcg cgcagccgtc gcggcatctg accgtgggtt ccagaaatt      1800 cgtgggtgtc gagatcgaga ccgaccgccc ccacggcgtg ccccgcccga tgatcatgga     1860
cgcgaccgtc acccagcagg acgggtaccg cttcatctat ctgctgccct tctctccgac     1920
gcgcatcctg atcgaggaca cgcgctattc cgatggcggc gatctggacg acgacgcgct     1980
ggcggcgggg tcccacgact atgcccgcca gcagggctgg accggggccg aggtccggcg     2040
cgaacgcggc atccttccca tcgcgctggc ccatgatgcg gcgggcttct gggccgatca     2100
cgcggcgggg cctgttcccg tgggactgcg cgcggggttc tttcatccgg tcaccggcta     2160
ttcgctgccc tatgcggcac aggtggcgga cgtggtggcg ggtctgtccg ggccgcccgg     2220
caccgacgcg ctgcgcggcg ccatccgcga ttacgcgatc gaccgggcgc gccgcgaccg     2280
cttcctgcgc cttttgaacc ggatgctgtt ccgcggctgc gcgcccgacc ggcgctatac     2340
cctgctgcag cggttctacc gcatgccgca tggactgatc gaacggttct atgccggccg     2400
gctgagcgtg gcggatcagc tgcgcatcgt gaccggcaag cctcccattc cccttggcac     2460
ggccatccgc tgcctgcccg aacgtcccct gctgaaggaa aacgcatgaa cgcccattcg     2520
cccgcggcca agaccgccat cgtgatcggc gcaggctttg gcgggctggc cctggccatc     2580
cgcctgcagt ccgcgggcat cgccaccacc ctggtcgagg cccgggacaa gcccggcggg     2640
cgcgcctatg tctggcacga tcagggccat ctcttcgacg cgggcccgac cgtcatcacc     2700
gaccccgatg cgctgaaaga gctgtgggcc ctgaccgggc aggacatggc gcgcgacgtg     2760
acgctgatgc cggtctcgcc cttctatcgg ctgatgtggc cgggcgggaa ggtcttcgat     2820
tacgtgaacg aggccgatca gctggaacgc cagatcgccc agttcaaccc ggacgacctg     2880
gagggatacc gccgcttccg tgattacgct gaggaggtgt accaggaggg ctacgtcaag     2940
ctgggcaccg tgcccttcct caagctgggc cagatgctca aggccgcgcc cgcgctgatg     3000
aagttggagg cctacaagtc ggtccatgcc aaggtcgcga ccttcatcaa ggaccccat      3060 ctgcggcagg cgtttcgta tcacacgctg ctggtgggcg ggaatccctt ctcgaccagc     3120
tcgatctatg cgctgaacca cgcgctggag cggcgcggcg gggtctggtt cgccaagggc     3180
```

```
ggcaccaacc agctggttgc gggcatggtc gcgctgttcg aacggcttgg cgggcagatg    3240
ctgctaaacg ccaaggtcgc gcggatcgac acggacgggc cgcgcgcgac cggcgtgacc    3300
ctggccgacg ggcgcgcctt gaccgccgac atggtcgcca gcaacggcga cgtgatgcac    3360
aactatcgcg acctgctggg ccataccgcc cgcgggcaga gccgggcgaa atcgctgaac    3420
gcgaagcgct ggtccatgtc gctcttcgtg ctgcatttcg gcctgcgcga ggcgcccaag    3480
gacgtggcgc atcacaccat cctgttcggc ccccgctaca aggagctggt caacgagatc    3540
ttcaagggcc cgaagctggc cgaggatttc tcgctctatc tgcattcgcc ctgcacgacc    3600
gacccggaga tggcgcctcc gggcatgtcc acgcattacg tcctggcccc ggtgccgcat    3660
ctgggccgcg cggacattga ttgggcggtc gaggggccgc gctatgccga ccgcatcctg    3720
gccagcctgg aggagcggct gatcccgaac ctgcgcgcca acctgaccac gacgcgcatc    3780 ttcacccgt ccgatttcgc cagcgaactg aacgcccatc atggcagcgc cttctcggtc    3840
gagccgatcc tgacgcaatc cgcgtggttc cggccgcaca accgcgacaa gacgatccgc    3900
aacttctatc tggtcggcgc gggcacccat ccgggcgcgg ggattccggg cgtcgtgggc    3960
tcggccaagg ccacgcccca ggtgatgctg tccgacctgg cgagcgcatg agcgatctgg    4020
tcctgacctc gaccgaggcg atcacccaag ggtcgcaaag ctttgccacg gcggccaagc    4080
tgatgccgcc gggcatccgc gacgacacgg tgatgctcta tgcctggtgc gccacgcgg    4140 atgacgtgat cgacggtcag gccctgggca gctgccccga ggcggtgaac gacccgcagg    4200
cgcggctgga cggcctgcgc gccgacacgc tggccgcgtt gcagggcgac ggtccggtga    4260
ccccgccctt tgcctgcgcg gtggcgcggc ggcatgattt tccgcaggcc tggcccatgg    4320
acctgatcga aggctttgcg atggatgtcg aggcgcgcga ctatcgcacg ctggacgacg    4380
tgctggaata ttcctatcac gtcgcgggca tcgtcggcgt gatgatggcc cgtgtgatgg    4440
gcgtgcgcga cgatcctgtc ctggaccgtg cctgcgacct ggggctggcg ttccagctga    4500
ccaacatcgc gcgcgacgtg atcgacgacg cgcgcatcgg gcggtgctat ctgccaggcg    4560
actggctgga tcaggcgggc gcgcgggtcg acgggccggt gccgtcgccg gagctgtaca    4620
ccgtgatcct gcgcctgctg gatgcggctg aactctatta cgcgtcggcg cgggtgggtc    4680
tggcggatct gccgccgcgc tgcgcctggt ccatcgccgc cgcgttgcgg atctatcgcg    4740
ccatcgggct cgcatccgc aagggcgggc cggaggccta tcgccagcgg atcagcacgt    4800
ccaaggccgc caagatcggg ctgctgggca tcggggctg ggatgtcgcc gatcacgcct    4860
gccgggggcg cgcgtgtcgcg acaggcctct ggacccggcc gcatcacgcc taggcgcgcg    4920
cggcgtaggg cagaacccgt tccagcaggg ccgcgatttc cggagcctga aggcgcttgc    4980
tgcgcagcat cgcgtccagc tgggcgcggc tggcctcata gtggcgggac acgttctgca    5040
ggtctgacac ggccagaagg ccgcgccgcg ggccggggc cgcggcatcg cgaccggtat    5100
ccttgccaag cgccgcctgg tcgcccacga cgtccagcag gtcgtcatag gactggaaca    5160
cccggcccag ctgacggcca aagtcgatca tctgggtctg ctcctcggcg tcgaactcct    5220
tgatcacggc cagcgtctcc agcccggcga tgaacagcac gccggtcttc aggtcctgtt    5280
cctgttcgac ccccgcgccg ttcttggccg cgtgcaggtc caggtcctgg ccggcgcaca    5340
ggccctgcgg ccccagggac cgcgacagga tccgcaccag ctgcgcccgc ccgtgcccg    5400 acgcgccgcg cgcaccggcc agcagggcca tcgcctcggt gatcagggcg atgccgccca    5460
gcacggcgcg gctttcgcca tgcgccacat gggtcgcgga ctggccgcgg cgcagcccgg    5520
catcgtccat gcagggcagg tcgtcgaaga tcagcgatgc ggcatgcacc atctcgaccg    5580
```

```
cgcaggcggc gtcgacgatc gtgtcgcaga ccccgcccga ggcctctgcc gcaagcagca   5640
tcagcatgcc gcggaaccgc ttgcccgacg acagcgcgcc atggctcatg ccgcgccga    5700 gcggctgcga cacggcaccg aatccctggg cgatctcctc aagtctggtc tgcagaaggg   5760
tggcgtggat cgggttgacg tctcgtctca tcagtgccct cgcgctgggg ttctgacctg   5820
gcgggaaggt caggccgggg cggcaccccg tgacccgtca tccaccgtca acagtcccca   5880
tgttggaacg gttcacgccc gattgcgagc cttttcgacg gcgacgcggg gtcgcgcggc   5940
aatttgtcca acaaggtcag tggaccggcg cgccgatggc cgcgcgcagc caggcatcct   6000
tggccggaaa caccccgcgc cgcatcatga tcggccagga tcgtccggcg cggcgcggc    6060 gcaggtcggc cgcgtcaccc ggattgtcaa gcacccaggc catcgcatcc gcgacctcgt   6120
ccgcgtcgtc catgtcgacg atcaggccgt tctccatgtc gcggaccagt tcgcgcaccg   6180 ggcggtgtt cgatccgatc accaggcacc cggtggccat cgcctcggac agggaccagg    6240
aggtgacgaa gggctcggtg aaatagacat gtgcgtgcga ggcctgcagc gtgcggacat   6300
attcatcgcg cgggcgcatg gcgttcacgt ggatgcggcg gtggtccagg tccagctggt   6360
cgatcatccg cagccaccag ccgtcgccgc gcgccagcgg tcgaccatag gacacgctgt   6420
cattggccag gatcaccgtg ccgaagtcgt cacgccgcgc ctgcaggcgg gcgacgccgc   6480
gcaggaattg cggaaagccg cgcaagggct ccatcccgcg gtggtatag gtgatcacgg     6540 ggcggtcggc gggcaggcgc agccagtcga atcgatgcg cgcctgcggg tcggggcggt    6600
gcaggtcgca atcgaccccca tccggcatca cggtgatctg gcggcgcagg accggaggaa   6660
agcggctggc ctggaacagc gtcgggcacc agctggcatc ggccaggtcg aattcgccgg   6720
tgatcggcag gttgcgcatc cggtccgaga tcatcaccgc caggtcggcg gcttttccg     6780 cccggcgctt gtcccagttg cggtcggtgt aataccattc gtgataggcg acataggtgc   6840
agtccggcca gaccagcttg accccccagcc ccacgcccca gcccgcatgg ccaccacga   6900 cgtccgggac atagccttcg gaatggcgca tgcggaacat cagctcggtc gcgccccggc   6960
agttctgcgc ggcgtggtcc aggatgtgac gcggatcgcc cgtggggatc gtggtgtcgc   7020 gcancgcga                                                          7029
```

<210> SEQ ID NO 2
<211> LENGTH: 242
<212> TYPE: PRT
<213> ORGANISM: Paracoccus sp.

<400> SEQUENCE: 2

```
Met Ser Ala His Ala Leu Pro Lys Ala Asp Leu Thr Ala Thr Ser Leu
1               5                   10                  15

Ile Val Ser Gly Gly Ile Ile Ala Ala Trp Leu Ala Leu His Val His
            20                  25                  30

Ala Leu Trp Phe Leu Asp Ala Ala Ala His Pro Ile Leu Ala Ile Ala
        35                  40                  45

Asn Phe Leu Gly Leu Thr Trp Leu Ser Val Gly Leu Phe Ile Ile Ala
    50                  55                  60

His Asp Ala Met His Gly Ser Val Val Pro Gly Arg Pro Arg Ala Asn
65                  70                  75                  80

Ala Ala Met Gly Gln Leu Val Leu Trp Leu Tyr Ala Gly Phe Ser Trp
                85                  90                  95

Arg Lys Met Ile Val Lys His Met Ala His Arg His Ala Gly Thr
            100                 105                 110
```

```
Asp Asp Asp Pro Asp Phe Asp His Gly Gly Pro Val Arg Trp Tyr Ala
        115                 120                 125

Arg Phe Ile Gly Thr Tyr Phe Gly Trp Arg Glu Gly Leu Leu Leu Pro
130                 135                 140

Val Ile Val Thr Val Tyr Ala Leu Ile Leu Gly Asp Arg Trp Met Tyr
145                 150                 155                 160

Val Val Phe Trp Pro Leu Pro Ser Ile Leu Ala Ser Ile Gln Leu Phe
                165                 170                 175

Val Phe Gly Thr Trp Leu Pro His Arg Pro Gly His Asp Ala Phe Pro
                180                 185                 190

Asp Arg His Asn Ala Arg Ser Ser Arg Ile Ser Asp Pro Val Ser Leu
            195                 200                 205

Leu Thr Cys Phe His Phe Gly Gly Tyr His His Glu His His Leu His
        210                 215                 220

Pro Thr Val Pro Trp Trp Arg Leu Pro Ser Thr Arg Thr Lys Gly Asp
225                 230                 235                 240

Thr Ala
```

```
<210> SEQ ID NO 3
<211> LENGTH: 162
<212> TYPE: PRT
<213> ORGANISM: Paracoccus sp.

<400> SEQUENCE: 3

Met Thr Asn Phe Leu Ile Val Val Ala Thr Val Leu Val Met Glu Leu
1               5                   10                  15

Thr Ala Tyr Ser Val His Arg Trp Ile Met His Gly Pro Leu Gly Trp
            20                  25                  30

Gly Trp His Lys Ser His His Glu His Asp His Ala Leu Glu Lys
        35                  40                  45

Asn Asp Leu Tyr Gly Leu Val Phe Ala Val Ile Ala Thr Val Leu Phe
    50                  55                  60

Thr Val Gly Trp Ile Trp Ala Pro Val Leu Trp Trp Ile Ala Leu Gly
65                  70                  75                  80

Met Thr Val Tyr Gly Leu Ile Tyr Phe Val Leu His Asp Gly Leu Val
                85                  90                  95

His Gln Arg Trp Pro Phe Arg Tyr Ile Pro Arg Lys Gly Tyr Ala Arg
            100                 105                 110

Arg Leu Tyr Gln Ala His Arg Leu His His Ala Val Glu Gly Arg Asp
        115                 120                 125

His Cys Val Ser Phe Gly Phe Ile Tyr Ala Pro Pro Val Asp Lys Leu
    130                 135                 140

Lys Gln Asp Leu Lys Met Ser Gly Val Leu Arg Ala Glu Ala Gln Glu
145                 150                 155                 160

Arg Thr
```

```
<210> SEQ ID NO 4
<211> LENGTH: 386
<212> TYPE: PRT
<213> ORGANISM: Paracoccus sp.

<400> SEQUENCE: 4

Met Thr His Asp Val Leu Leu Ala Gly Ala Gly Leu Ala Asn Gly Leu
1               5                   10                  15

Ile Ala Leu Ala Leu Arg Ala Ala Arg Pro Asp Leu Arg Val Leu Leu
```

```
            20                  25                  30
Leu Asp His Ala Ala Gly Pro Ser Asp Gly His Thr Trp Ser Cys His
            35                  40                  45

Asp Pro Asp Leu Ser Pro Asp Trp Leu Ala Arg Leu Lys Pro Leu Arg
        50                  55                  60

Arg Ala Asn Trp Pro Asp Gln Glu Val Arg Phe Pro Arg His Ala Arg
65                  70                  75                  80

Arg Leu Ala Thr Gly Tyr Gly Ser Leu Asp Gly Ala Ala Leu Ala Asp
                85                  90                  95

Ala Val Val Arg Ser Gly Ala Glu Ile Arg Trp Asp Ser Asp Ile Ala
            100                 105                 110

Leu Leu Asp Ala Gln Gly Ala Thr Leu Ser Cys Gly Thr Arg Ile Glu
            115                 120                 125

Ala Gly Ala Val Leu Asp Gly Arg Gly Ala Gln Pro Ser Arg His Leu
            130                 135                 140

Thr Val Gly Phe Gln Lys Phe Val Gly Val Glu Ile Glu Thr Asp Arg
145                 150                 155                 160

Pro His Gly Val Pro Arg Pro Met Ile Met Asp Ala Thr Val Thr Gln
                165                 170                 175

Gln Asp Gly Tyr Arg Phe Ile Tyr Leu Leu Pro Phe Ser Pro Thr Arg
                180                 185                 190

Ile Leu Ile Glu Asp Thr Arg Tyr Ser Asp Gly Gly Asp Leu Asp Asp
            195                 200                 205

Asp Ala Leu Ala Ala Ala Ser His Asp Tyr Ala Arg Gln Gln Gly Trp
            210                 215                 220

Thr Gly Ala Glu Val Arg Arg Glu Arg Gly Ile Leu Pro Ile Ala Leu
225                 230                 235                 240

Ala His Asp Ala Ala Gly Phe Trp Ala Asp His Ala Ala Gly Pro Val
                245                 250                 255

Pro Val Gly Leu Arg Ala Gly Phe Phe His Pro Val Thr Gly Tyr Ser
                260                 265                 270

Leu Pro Tyr Ala Ala Gln Val Ala Asp Val Val Ala Gly Leu Ser Gly
            275                 280                 285

Pro Pro Gly Thr Asp Ala Leu Arg Gly Ala Ile Arg Asp Tyr Ala Ile
            290                 295                 300

Asp Arg Ala Arg Asp Arg Phe Leu Arg Leu Leu Asn Arg Met Leu
305                 310                 315                 320

Phe Arg Gly Cys Ala Pro Asp Arg Arg Tyr Thr Leu Leu Gln Arg Phe
                325                 330                 335

Tyr Arg Met Pro His Gly Leu Ile Glu Arg Phe Tyr Ala Gly Arg Leu
                340                 345                 350

Ser Val Ala Asp Gln Leu Arg Ile Val Thr Gly Lys Pro Pro Ile Pro
            355                 360                 365

Leu Gly Thr Ala Ile Arg Cys Leu Pro Glu Arg Pro Leu Leu Lys Glu
            370                 375                 380

Asn Ala
385

<210> SEQ ID NO 5
<211> LENGTH: 501
<212> TYPE: PRT
<213> ORGANISM: Paracoccus sp.

<400> SEQUENCE: 5
```

```
Met Asn Ala His Ser Pro Ala Ala Lys Thr Ala Ile Val Ile Gly Ala
1               5                   10                  15
Gly Phe Gly Gly Leu Ala Leu Ala Ile Arg Leu Gln Ser Ala Gly Ile
            20                  25                  30
Ala Thr Thr Leu Val Glu Ala Arg Asp Lys Pro Gly Gly Arg Ala Tyr
                35                  40                  45
Val Trp His Asp Gln Gly His Leu Phe Asp Ala Gly Pro Thr Val Ile
        50                  55                  60
Thr Asp Pro Asp Ala Leu Lys Glu Leu Trp Ala Leu Thr Gly Gln Asp
65                  70                  75                  80
Met Ala Arg Asp Val Thr Leu Met Pro Val Ser Pro Phe Tyr Arg Leu
                85                  90                  95
Met Trp Pro Gly Gly Lys Val Phe Asp Tyr Val Asn Glu Ala Asp Gln
            100                 105                 110
Leu Glu Arg Gln Ile Ala Gln Phe Asn Pro Asp Asp Leu Glu Gly Tyr
                115                 120                 125
Arg Arg Phe Arg Asp Tyr Ala Glu Glu Val Tyr Gln Glu Gly Tyr Val
        130                 135                 140
Lys Leu Gly Thr Val Pro Phe Leu Lys Leu Gly Gln Met Leu Lys Ala
145                 150                 155                 160
Ala Pro Ala Leu Met Lys Leu Glu Ala Tyr Lys Ser Val His Ala Lys
                165                 170                 175
Val Ala Thr Phe Ile Lys Asp Pro Tyr Leu Arg Gln Ala Phe Ser Tyr
            180                 185                 190
His Thr Leu Leu Val Gly Gly Asn Pro Phe Ser Thr Ser Ser Ile Tyr
        195                 200                 205
Ala Leu Ile His Ala Leu Glu Arg Arg Gly Gly Val Trp Phe Ala Lys
    210                 215                 220
Gly Gly Thr Asn Gln Leu Val Ala Gly Met Val Ala Leu Phe Glu Arg
225                 230                 235                 240
Leu Gly Gly Gln Met Leu Leu Asn Ala Lys Val Ala Arg Ile Asp Thr
                245                 250                 255
Asp Gly Pro Arg Ala Thr Gly Val Thr Leu Ala Asp Gly Arg Ala Leu
            260                 265                 270
Thr Ala Asp Met Val Ala Ser Asn Gly Asp Val Met His Asn Tyr Arg
        275                 280                 285
Asp Leu Leu Gly His Thr Ala Arg Gly Gln Ser Arg Ala Lys Ser Leu
    290                 295                 300
Asn Ala Lys Arg Trp Ser Met Ser Leu Phe Val Leu His Phe Gly Leu
305                 310                 315                 320
Arg Glu Ala Pro Lys Asp Val Ala His His Thr Ile Leu Phe Gly Pro
                325                 330                 335
Arg Tyr Lys Glu Leu Val Asn Glu Ile Phe Lys Gly Pro Lys Leu Ala
            340                 345                 350
Glu Asp Phe Ser Leu Tyr Leu His Ser Pro Cys Thr Thr Asp Pro Glu
        355                 360                 365
Met Ala Pro Pro Gly Met Ser Thr His Tyr Val Leu Ala Pro Val Pro
    370                 375                 380
His Leu Gly Arg Ala Asp Ile Asp Trp Ala Val Glu Gly Pro Arg Tyr
385                 390                 395                 400
Ala Asp Arg Ile Leu Ala Ser Leu Glu Glu Arg Leu Ile Pro Asn Leu
                405                 410                 415
Arg Ala Asn Leu Thr Thr Thr Arg Ile Phe Thr Pro Ser Asp Phe Ala
```

```
                    420                 425                 430
Ser Glu Leu Asn Ala His His Gly Ser Ala Phe Ser Val Glu Pro Ile
            435                 440                 445

Leu Thr Gln Ser Ala Trp Phe Arg Pro His Asn Arg Asp Lys Thr Ile
        450                 455                 460

Arg Asn Phe Tyr Leu Val Gly Ala Gly Thr His Pro Gly Ala Gly Ile
465                 470                 475                 480

Pro Gly Val Val Gly Ser Ala Lys Ala Thr Ala Gln Val Met Leu Ser
                485                 490                 495

Asp Leu Ala Ser Ala
            500

<210> SEQ ID NO 6
<211> LENGTH: 304
<212> TYPE: PRT
<213> ORGANISM: Paracoccus sp.

<400> SEQUENCE: 6

Met Ser Asp Leu Val Leu Thr Ser Thr Glu Ala Ile Thr Gln Gly Ser
1               5                   10                  15

Gln Ser Phe Ala Thr Ala Ala Lys Leu Met Pro Pro Gly Ile Arg Asp
            20                  25                  30

Asp Thr Val Met Leu Tyr Ala Trp Cys Arg His Ala Asp Asp Val Ile
        35                  40                  45

Asp Gly Gln Ala Leu Gly Ser Arg Pro Glu Ala Val Asn Asp Pro Gln
    50                  55                  60

Ala Arg Leu Asp Gly Leu Arg Ala Asp Thr Leu Ala Ala Leu Gln Gly
65                  70                  75                  80

Asp Gly Pro Val Thr Pro Pro Phe Ala Ala Leu Arg Ala Val Ala Arg
                85                  90                  95

Arg His Asp Phe Pro Gln Ala Trp Pro Met Asp Leu Ile Glu Gly Phe
            100                 105                 110

Ala Met Asp Val Glu Ala Arg Asp Tyr Arg Thr Leu Asp Asp Val Leu
        115                 120                 125

Glu Tyr Ser Tyr His Val Ala Gly Ile Val Gly Val Met Met Ala Arg
    130                 135                 140

Val Met Gly Val Arg Asp Asp Pro Val Leu Asp Arg Ala Cys Asp Leu
145                 150                 155                 160

Gly Leu Ala Phe Gln Leu Thr Asn Ile Ala Arg Asp Val Ile Asp Asp
                165                 170                 175

Ala Arg Ile Gly Arg Cys Tyr Leu Pro Gly Asp Trp Leu Asp Gln Ala
            180                 185                 190

Gly Ala Arg Val Asp Gly Pro Val Pro Ser Pro Glu Leu Tyr Thr Val
        195                 200                 205

Ile Leu Arg Leu Leu Asp Ala Ala Glu Leu Tyr Tyr Ala Ser Ala Arg
    210                 215                 220

Val Gly Leu Ala Asp Leu Pro Pro Arg Cys Ala Trp Ser Ile Ala Ala
225                 230                 235                 240

Ala Leu Arg Ile Tyr Arg Ala Ile Gly Leu Arg Ile Arg Lys Gly Gly
                245                 250                 255

Pro Glu Ala Tyr Arg Gln Arg Ile Ser Thr Ser Lys Ala Ala Lys Ile
            260                 265                 270

Gly Leu Leu Gly Ile Gly Gly Trp Asp Val Ala Arg Ser Arg Leu Pro
        275                 280                 285
```

```
Gly Ala Gly Val Ser Arg Gln Gly Leu Trp Thr Arg Pro His His Ala
        290                 295                 300

<210> SEQ ID NO 7
<211> LENGTH: 293
<212> TYPE: PRT
<213> ORGANISM: Paracoccus sp.

<400> SEQUENCE: 7

Met Arg Arg Asp Val Asn Pro Ile His Ala Thr Leu Leu Gln Thr Arg
1               5                   10                  15

Leu Glu Glu Ile Ala Gln Gly Phe Gly Ala Val Ser Gln Pro Leu Gly
            20                  25                  30

Ala Ala Met Ser His Gly Ala Leu Ser Ser Gly Lys Arg Phe Arg Gly
        35                  40                  45

Met Leu Met Leu Leu Ala Ala Glu Ala Ser Gly Gly Val Cys Asp Thr
    50                  55                  60

Ile Val Asp Ala Ala Cys Ala Val Glu Met Val His Ala Ala Ser Leu
65                  70                  75                  80

Ile Phe Asp Asp Leu Pro Cys Met Asp Asp Ala Gly Leu Arg Arg Gly
                85                  90                  95

Gln Ser Ala Thr His Val Ala His Gly Glu Ser Arg Ala Val Leu Gly
            100                 105                 110

Gly Ile Ala Leu Ile Thr Glu Ala Met Ala Leu Leu Ala Gly Ala Arg
        115                 120                 125

Gly Ala Ser Gly Thr Gly Arg Ala Gln Leu Val Arg Ile Leu Ser Arg
    130                 135                 140

Ser Leu Gly Pro Gln Gly Leu Cys Ala Gly Gln Asp Leu Asp Leu His
145                 150                 155                 160

Ala Ala Lys Asn Gly Ala Gly Val Glu Gln Glu Gln Asp Leu Lys Thr
                165                 170                 175

Gly Val Leu Phe Ile Ala Gly Leu Glu Thr Leu Ala Val Ile Lys Glu
            180                 185                 190

Phe Asp Ala Glu Glu Gln Thr Gln Met Ile Asp Phe Gly Arg Gln Leu
        195                 200                 205

Gly Arg Val Phe Gln Ser Tyr Asp Asp Leu Leu Asp Val Val Gly Asp
    210                 215                 220

Gln Ala Ala Leu Gly Lys Asp Thr Gly Arg Asp Ala Ala Pro Gly
225                 230                 235                 240

Pro Arg Arg Gly Leu Leu Ala Val Ser Asp Leu Gln Asn Val Ser Arg
                245                 250                 255

His Tyr Glu Ala Ser Arg Ala Gln Leu Asp Ala Met Leu Arg Ser Lys
            260                 265                 270

Arg Leu Gln Ala Pro Glu Ile Ala Leu Leu Glu Arg Val Leu Pro
        275                 280                 285

Tyr Ala Ala Arg Ala
    290

<210> SEQ ID NO 8
<211> LENGTH: 5377
<212> TYPE: DNA
<213> ORGANISM: Paracoccus sp.

<400> SEQUENCE: 8
gcggatccgg cgaccttgcg gcgctgcgcc gcgcgccttt gctggtgcct gggccgggtg      60
gccaatggtc gcaagcaacg ggatggaaaa ccggcgatgc gggactgtag tctgcgcgga     120
```

| | | |
|---|---|---|
| tcgccggtcc gggggacaag atgagccgcac atgccctgcc caaggcagat ctgaccgcca | 180 |
| ccagcctgat cgtctcgggc ggcatcatcg ccgcttggct ggccctgcat gtgcatgcgc | 240 |
| tgtggtttct ggacgcagcg gcgcatccca tcctggcgat cgcaaatttc ctggggctga | 300 |
| cctggctgtc ggtcggattg ttcatcatcg cgcatgacgc gatgcacggg tcggtggtgc | 360 |
| cggggcgtcc gcgcgccaat gcggcgatgg ccagcttgt cctgtggctg tatgccggat | 420 |
| tttcgtggcg caagatgatc gtcaagcaca tggcccatca ccgccatgcc ggaaccgacg | 480 |
| acgaccccga tttcgaccat ggcggcccgg tccgctggta cgcccgcttc atcggcacct | 540 |
| atttcggctg gcgcgagggg ctgctgctgc ccgtcatcgt gacggtctat gcgctgatcc | 600 |
| ttggggatcg ctggatgtac gtggtcttct ggccgctgcc gtcgatcctg cgtcgatcc | 660 |
| agctgttcgt gttcggcacc tggctgccgc accgccccgg ccacgacgcg ttcccggacc | 720 |
| gccacaatgc gcggtcgtcg cggatcagcg accccgtgtc gctgctgacc tgctttcact | 780 |
| ttggcggtta tcatcacgaa caccacctgc accgacggt gccgtggtgg cgcctgccca | 840 |
| gcacccgcac caaggggggac accgcatgac caatttcctg atcgtcgtcg ccaccgtgct | 900 |
| ggtgatggag ttgacggcct attccgtcca ccgctggatc atgcacggcc cctgggctg | 960 |
| gggctggcac aagtcccacc acgaggaaca cgaccacgcg ctggaaaaga acgacctgta | 1020 |
| cggcctggtc tttgcggtga tcgccacggt gctgttcacg gtgggctgga tctgggcgcc | 1080 |
| ggtcctgtgg tggatcgcct ggggcatgac tgtctatggg ctgatctatt tcgtcctgca | 1140 |
| tgacgggctg gtgcatcagc gctggccgtt ccgttatatc ccgcgcaagg gctatgccag | 1200 |
| acgcctgtat caggcccacc gcctgcacca tgcggtcgag gggcgcgacc attgcgtcag | 1260 |
| cttcggcttc atctatgcgc ccccggtcga caagctgaag caggacctga agatgtcggg | 1320 |
| cgtgctgcgg gccgaggcgc aggagcgcac gtgacccatg acgtgctgct ggcaggggcg | 1380 |
| ggccttgcca acgggctgat cgccctggcg ctgcgcgcgg cgcggcccga cctgcgcgtg | 1440 |
| ctgctgctgg accatgccgc aggaccgtca gacggccaca cctggtcctg ccacgacccc | 1500 |
| gacctgtcgc cggactggct ggcgcggctg aagcccctgc gccgcgccaa ctggcccgac | 1560 |
| caggaggtgc gctttccccg ccatgcccgg cggctggcca ccggttacgg gtcgctggac | 1620 |
| ggggcggcgc tggcggatgc ggtggtccgg tcgggcgccg agatccgctg ggacagcgac | 1680 |
| atcgccctgc tggatgcgca gggggcgacg ctgtcctgcg gcacccggat cgaggcgggc | 1740 |
| gcggtcctgg acgggcgggg cgcgcagccg tcgcggcatc tgaccgtggg tttccagaaa | 1800 |
| ttcgtgggtg tcgagatcga gaccgaccgc ccccacggcg tgccccgccc gatgatcatg | 1860 |
| gacgcgaccg tcacccagca ggacgggtac cgcttcatct atctgctgcc cttctctccg | 1920 |
| acgcgcatcc tgatcgagga cacgcgctat ccgatggcg gcgatctgga cgacgacgcg | 1980 |
| ctggcggcgg cgtcccacga ctatgcccgc cagcagggct ggaccggggc cgaggtccgg | 2040 |
| cgcgaacgcg gcatccttcc catcgcgctg gcccatgatg cggcgggctt ctgggccgat | 2100 |
| cacgcggcgg ggcctgttcc cgtgggactg cgcgcggggt tctttcatcc ggtcaccggc | 2160 |
| tattcgctgc cctatgcggc acaggtggcg gacgtggtgg cgggtctgtc cgggccgccc | 2220 |
| ggcaccgacg cgctgcgcgg cgccatccgc gattacgcga tcgaccgggc gcgccgcgac | 2280 |
| cgctttctgc gccttttgaa ccggatgctg ttccgcggct gcgcgcccga ccggcgctat | 2340 |
| accctgctgc agcggttcta ccgcatgccg catggactga tcgaacggtt ctatgccggc | 2400 |
| cggctgagcg tggcggatca gctgcgcatc gtgaccggca agcctcccat tcccttggc | 2460 |

```
acggccatcc gctgcctgcc cgaacgtccc ctgctgaagg aaaacgcatg aacgcccatt    2520
cgcccgcggc caagaccgcc atcgtgatcg gcgcaggctt tggcgggctg ccctggcca     2580 tccgcctgca gtccgcgggc atcgccacca ccctggtcga ggcccgggac aagcccggcg    2640
ggcgcgccta tgtctggcac gatcagggcc atctcttcga cgcgggcccg accgtcatca    2700
ccgaccccga tgcgctgaaa gagctgtggg ccctgaccgg gcaggacatg gcgcgcgacg    2760
tgacgctgat gccggtctcg cccttctatc ggctgatgtg gccgggcggg aaggtcttcg    2820
attacgtgaa cgaggccgat cagctggaac gccagatcgc ccagttcaac ccggacgacc    2880
tggagggata ccgccgcttc cgtgattacg ctgaggaggt gtaccaggag gctacgtca     2940 agctgggcac cgtgcccttc ctcaagctgg gccagatgct caaggccgcg cccgcgctga    3000
tgaagttgga ggcctacaag tcggtccatg ccaaggtcgc gaccttcatc aaggacccct    3060
atctgcggca ggcgttttcg tatcacacgc tgctggtggg cgggaatccc ttctcgacca    3120
gctcgatcta tgcgctgaac cacgcgctgg agcggcgcgg cggggtctgg ttcgccaagg    3180
gcggcaccaa ccagctggtt gcgggcatgg tcgcgctgtt cgaacggctt ggcgggcaga    3240
tgctgctaaa cgccaaggtc gcgcggatcg acacggacgg gccgcgcgcg accggcgtga    3300
ccctggccga cgggcgcgcc ttgaccgccg acatggtcgc cagcaacggc gacgtgatgc    3360
acaactatcg cgacctgctg ggccataccg cccgcgggca gagccgggcg aaatcgctga    3420
acgcgaagcg ctggtccatg tcgctcttcg tgctgcattt cggcctgcgc gaggcgccca    3480
aggacgtggc gcatcacacc atcctgttcg gccccgcta caaggagctg gtcaacgaga    3540
tcttcaaggg cccgaagctg gccgaggatt tctcgctcta tctgcattcg ccctgcacga    3600
ccgacccgga gatggcgcct ccgggcatgt ccacgcatta cgtcctggcc ccggtgccgc    3660
atctgggccg cgcggacatt gattgggcgg tcgaggggcc gcgctatgcc gaccgcatcc    3720
tggccagcct ggaggagcgg ctgatcccga acctgcgcgc caacctgacc acgacgcgca    3780
tcttcacccc gtccgatttc gccagcgaac tgaacgccca tcatggcagc gccttctcgg    3840
tcgagccgat cctgacgcaa tccgcgtggt tccgccgca caaccgcgac aagacgatcc    3900
gcaacttcta tctggtcggc gcgggcaccc atccgggcgc ggggattccg ggcgtcgtgg    3960
gctcggccaa ggccacggcc caggtgatgc tgtccgacct ggcgagcgca tgagcgatct    4020
ggtcctgacc tcgaccgagg cgatcaccca agggtcgcaa agctttgcca cggcggccaa    4080
gctgatgccg ccgggcatcc gcgacgacac ggtgatgctc tatgcctggt gccgccacgc    4140
ggatgacgtg atcgacggtc aggccctggg cagctgcccc gaggcggtga acgacccgca    4200
ggcgcggctg gacggcctgc gcgccgacac gctggccgcg ttgcagggcg acggtccggt    4260
gaccccgccc tttgcctgcg cggtggcgcg gcggcatgat tttccgcagg cctggcccat    4320
ggacctgatc gaaggctttg cgatggatgt cgaggcgcgc gactatcgca cgctggacga    4380
cgtgctggaa tattcctatc acgtcgcggg catcgtcggc gtgatgatgg cccgtgtgat    4440
gggcgtgcgc gacgatcctg tcctggaccg tgcctgcgac ctggggctgg cgttccagct    4500
gaccaacatc gcgcgcgacg tgatcgacga cgcgcgcatc gggcggtgct atctgccagg    4560
cgactggctg gatcaggcgg gcgcgcgggt cgacgggccg gtgccgtcgc cggagctgta    4620
caccgtgatc ctgcgcctgc tggatgcggc tgaactctat tacgcgtcgg cgcgggtggg    4680
tctggcggat ctgccgccgc gctgcgcctg gtccatcgcc gccgcgttgc ggatctatcg    4740
cgccatcggc ctgcgcatcc gcaagggcgg gccgaggcc tatcgccagc ggatcagcac    4800
gtccaaggcc gccaagatcg ggctgctggg catcggggc tgggatgtcg ccgatcacgc    4860
```

```
ctgccggggg cggcgtgtcg cgacaggcct ctggacccgg ccgcatcacg cctaggcgcg     4920
cgcggcgtag ggcagaaccc gttccagcag ggccgcgatt tccggagcct gaaggcgctt     4980
gctgcgcagc atcgcgtcca gctgggcgcg gctggcctca tagtggcggg acacgttctg     5040
caggtctgac acggccagaa ggccgcgccg cgggtcgggg gccgcggcat cgcgaccggt     5100
atccttgcca agcgccgcct ggtcgcccac gacgtccagc aggtcgtcat aggactggaa     5160
cacccggccc agctgacggc caaagtcgat catctgggtc tgctcctcgg cgtcgaactc     5220
cttgatcacg gccagcatct ccagcccggc gatgaacagc acgccggtct tcaggtcctg     5280
ttcctgttcg accccgcgc cgttcttggc cgcgtgcagg tccaggtcct ggccggcgca     5340
caggccctgc ggccccaggg accgcgacag gatcccg                             5377
```

<210> SEQ ID NO 9
<211> LENGTH: 1416
<212> TYPE: DNA
<213> ORGANISM: Paracoccus sp.

<400> SEQUENCE: 9

```
gcggatccgg cgaccttgcg gcgctgcgcc gcgcgccttt gctggtgcct gggccgggtg       60
gccaatggtc gcaagcaacg gggatggaaa ccggcgatgc gggactgtag tctgcgcgga      120
tcgccggtcc gggggacaag atgagcgcac atgccctgcc caaggcagat ctgaccgcca      180
ccagcctgat cgtctcgggc ggcatcatcg ccgcttggct ggccctgcat gtgcatgcgc      240
tgtggtttct ggacgcagcg gcgcatccca tcctggcgat cgcaaatttc ctggggctga      300
cctggctgtc ggtcggattg ttcatcatcg cgcatgacgc gatgcacggg tcggtggtgc      360
cggggcgtcc gcgcgccaat gcggcgatgg ccagcttgt cctgtggctg tatgccggat      420
tttcgtggcg caagatgatc gtcaagcaca tggcccatca ccgccatgcc ggaaccgacg      480
acgaccccga tttcgaccat gcggccggg tccgctggta cgcccgcttc atcggcacct      540
atttcggctg gcgcgagggg ctgctgctgc ccgtcatcgt gacggtctat gcgctgatcc      600
ttggggatcg ctggatgtac gtggtcttct ggccgctgcc gtcgatcctg gcgtcgatcc      660
agctgttcgt gttcggcacc tggctgccgc accgccccgg ccacgacgcg ttcccggacc      720
gccacaatgc gcggtcgtcg cggatcagcg accccgtgtc gctgctgacc tgctttcact      780
ttggcggtta tcatcacgaa caccacctgc acccgacggt gccgtggtgg cgcctgccca      840
gcacccgcac caaggggac accgcatgac caatttcctg atcgtcgtcg ccaccgtgct      900
ggtgatggag ttgacggcct attccgtcca ccgctggatc atgcacggcc cctgggctg      960 gggctggcac aagtcccacc acgaggaaca cgaccacgcg ctggaaaaga acgacctgta     1020
cggcctggtc tttgcggtga tcgccacggt gctgttcacg gtgggctgga tctgggcgcc     1080
ggtcctgtgg tggatcgcct tgggcatgac tgtctatggg ctgatctatt tcgtcctgca     1140
tgacgggctg gtgcatcagc gctggccgtt ccgttatatc ccgcgcaagg gctatgccag     1200
acgcctgtat caggcccacc gcctgcacca tgcggtcgag gggcgcgacc attgcgtcag     1260
cttcggcttc atctatgcgc ccccggtcga caagctgaag caggacctga agatgtcggg     1320
cgtgctgcgg gccgaggcgc aggagcgcac gtgacccatg acgtgctgct ggcaggggcg     1380
ggccttgcca acgggctgat cgccctgcgg atcccg                              1416
```

<210> SEQ ID NO 10
<211> LENGTH: 1210
<212> TYPE: DNA

<213> ORGANISM: Paracoccus sp.

<400> SEQUENCE: 10

```
ctagtctaga tgcttgacaa tccgggtgac gcggccgacc tgcgccgcgc cgcgcgccgg      60
acgatcctgg ccgatcatga tgcggcgcgg gtgtttccgg ccaaggatgc ctggctgcgc     120
gcggccatcg gcgcgccggt ccactgacct tgttggacaa attgccgcgc gaccccgcgt     180
cgccgtcgaa aaggctcgca atcggcgtg aaccgttcca acatgggac tgttgacggt       240
ggatgacggg tcacggggtg ccgccccggc ctgaccttcc cgccaggtca gaaccccagc     300
gcgagggcac tgatgagacg agacgtcaac ccgatccacg ccaccttct gcagaccaga      360
cttgaggaga tcgcccaggg attcggtgcc gtgtcgcagc cgctcggcgc ggccatgagc     420
catggcgcgc tgtcgtcggg caagcggttc cgcggcatgc tgatgctgct tgcggcagag     480
gcctcgggcg gggtctgcga cacgatcgtc gacgccgcct gcgcggtcga gatggtgcat    540
gccgcatcgc tgatcttcga cgacctgccc tgcatggacg atgccgggct gcgccgcggc    600
cagtccgcga cccatgtggc gcatggcgaa agccgcgcc tgctgggcgg catcgccctg      660
atcaccgagg cgatggccct gctggccggt gcgcgcggcg cgtcgggcac ggggcgggcg    720
cagctggtgc ggatcctgtc gcggtccctg gggccgcagg gctgtgcgc cggccaggac     780
ctggacctgc acgcggccaa gaacggcgcg ggggtcgaac aggaacagga cctgaagacc    840
ggcgtgctgt tcatcgccgg gctggagacg ctggccgtga tcaaggagtt cgacgccgag    900
gagcagaccc agatgatcga ctttggccgt cagctgggcc gggtgttcca gtcctatgac    960
gacctgctgg acgtcgtggg cgaccaggcg gcgcttggca aggataccgg tcgcgatgcc   1020
gcggcccccg gccgcggcg cggccttctg gccgtgtcag acctgcagaa cgtgtcccgc   1080
cactatgagg ccagccgcgc ccagctggac gcgatgctgc gcagcaagcg ccttcaggct   1140
ccggaaatcg cggccctgct ggaacgggtt ctgccctacg ccgcgcgcgc ctaggcgtga   1200
tgagctccca                                                           1210
```

<210> SEQ ID NO 11
<211> LENGTH: 1086
<212> TYPE: DNA
<213> ORGANISM: Paracoccus sp.

<400> SEQUENCE: 11

```
ctagtctaga gccggtccac tgaccttgtt ggacaaattg ccgcgcgacc ccgcgtcgcc      60
gtcgaaaagg ctcgcaatcg ggcgtgaacc gttccaacat ggggactgtt gacggtggat    120
gacgggtcac ggggtgccgc cccggcctga ccttcccgcc aggtcagaac cccagcgcga    180
gggcactgat gagacgagac gtcaacccga tccacgccac ccttctgcag accagacttg    240
aggagatcgc ccagggattc ggtgccgtgt cgcagccgct cggcgcggcc atgagccatg    300
gcgcgctgtc gtcgggcaag cggttccgcg gcatgctgat gctgcttgcg gcagaggcct    360
cgggcggggt ctgcgacacg atcgtcgacg ccgcctgcgc ggtcgagatg gtgcatgccg    420
catcgctgat cttcgacgac ctgccctgca tggacgatgc cgggctgcgc cgcggccagt    480
ccgcgaccca tgtggcgcat ggcgaaagcc gcgccgtgct gggcggcatc gccctgatca    540
ccgaggcgat ggccctgctg gccggtgcgc gcggcgcgtc gggcacgggg cgggcgcagc    600
tggtgcggat cctgtcgcgg tccctggggc cgcagggcct gtgcgccggc caggacctgg    660
acctgcacgc ggccaagaac ggcgcggggg tcgaacagga acaggacctg aagaccggcg    720
tgctgttcat cgccgggctg gagacgctgg ccgtgatcaa ggagttcgac gccgaggagc    780
```

```
agacccagat gatcgacttt ggccgtcagc tgggccgggt gttccagtcc tatgacgacc      840
tgctggacgt cgtgggcgac caggcggcgc ttggcaagga taccggtcgc gatgccgcgg      900 ccccggccc gcggcgcggc cttctggccg tgtcagacct gcagaacgtg tcccgccact       960
atgaggccag ccgcgcccag ctggacgcga tgctgcgcag caagcgcctt caggctccgg     1020
aaatcgcggc cctgctggaa cgggttctgc cctacgccgc gcgcgcctag gcgtgatgag     1080
ctccca                                                                1086

<210> SEQ ID NO 12
<211> LENGTH: 6572
<212> TYPE: DNA
<213> ORGANISM: Paracoccus sp.

<400> SEQUENCE: 12
ctgtcgcggt ccctggggcc gcagggcctg tgcgccggcc aggacctgga cctgcacgcg       60
gccaagaacg cgcgggggt cgaacaggaa caggacctga agaccggcgt gctgttcatc       120
gccgggctgg agatgctggc cgtgatcaag gagttcgacg ccgaggagca gacccagatg      180
atcgactttg gccgtcagct gggccgggtg ttccagtcct atgacgacct gctggacgtc      240
gtgggcgacc aggcggcgct tggcaaggat accggtcgcg atgccgcggc ccccgacccg      300
cggcgcggcc ttctggccgt gtcagacctg cagaacgtgt cccgccacta tgaggccagc      360
cgcgcccagc tggacgcgat gctgcgcagc aagcgccttc aggctccgga aatcgcggcc      420
ctgctggaac gggttctgcc ctacgccgcg cgcgcctagg cgtgatgcgg ccgggtccag      480
aggcctgtcg cgacacgccg ccccggcag gcgtgatcgg cgacatccca gccccgatg       540 cccagcagcc cgatcttggc ggccttggac gtgctgatcc gctggcgata ggcctccggc      600
ccgcccttgc ggatgcgcag cccgatggcg cgatagatcc gcaacgcggc ggcgatggac      660
caggcgcagc gcggcggcag atccgccaga cccacccgcg ccgacgcgta atagagttca      720
gccgcatcca gcaggcgcag gatcacggtg tacagctccg gcgacggcac cggcccgtcg      780
acccgcgcgc ccgcctgatc cagccagtcg cctggcagat agcaccgccc gatgcgcgcg      840
tcgtcgatca cgtcgcgcgc gatgttggtc agctggaacg ccagcccag gtcgcaggca      900 cggtccagga caggatcgtc gcgcacgccc atcacacggg ccatcatcac gccgacgatg      960
cccgcgacgt gataggaata ttccagcacg tcgtccagcg tgcgatagtc gcgcgcctcg     1020
acatccatcg caaagccttc gatcaggtcc atgggccagg cctgcggaaa atcatgccgc     1080
cgcgccaccg cgcaggcaaa gggcggggtc accggaccgt cgccctgcaa gcggccagc      1140 gtgtcggcgc gcaggccgtc cagccgcgcc tgcgggtcgt tcaccgcctc ggggcagctg     1200
cccagggcct gaccgtcgat cacgtcatcc gcgtggcggc accaggcata gagcatcacc     1260
gtgtcgtcgc ggatgcccgg cggcatcagc ttggccgccg tggcaaagct ttgcgaccct     1320
tgggtgatcg cctcggtcga ggtcaggacc agatcgctca tgcgctcgcc aggtcggaca     1380
gcatcacctg ggccgtggcc ttggccgagc ccacgacgcc cggaatcccc gcgcccggat     1440
gggtgcccgc gccgaccaga tagaagttgc ggatcgtctt gtcgcggttg tgcggccgga     1500
accacgcgga ttgcgtcagg atcggctcga ccgagaaggc gctgccatga tgggcgttca     1560
gttcgctggc gaaatcggac ggggtgaaga tgcgcgtcgt ggtcaggttg gcgcgcaggt     1620
tcgggatcag ccgctcctcc aggctggcca ggatgcggtc ggcatagcgc ggcccctcga     1680
ccgcccaatc aatgtccgcg cggcccagat gcggcaccgg ggccaggacg taatgcgtgg     1740
```

```
acatgcccgg aggcgccatc tccgggtcgg tcgtgcaggg cgaatgcaga tagagcgaga   1800
aatcctcggc cagcttcggg cccttgaaga tctcgttgac cagctccttg tagcggggc    1860 cgaacaggat ggtgtgatgc gccacgtcct tgggcgcctc gcgcaggccg aaatgcagca   1920
cgaagagcga catggaccag cgcttcgcgt tcagcgattt cgcccggctc tgcccgcggg   1980
cggtatggcc cagcaggtcg cgatagttgt gcatcacgtc gccgttgctg gcgaccatgt   2040
cggcggtcaa ggcgcgcccg tcggccaggg tcacgccggt cgcgcgcggc ccgtccgtgt   2100
cgatccgcgc gaccttggcg tttagcagca tctgcccgcc aagccgttcg aacagcgcga   2160
ccatgcccgc aaccagctgg ttggtgccgc ccttggcgaa ccagaccccg ccgcgccgct   2220
ccagcgcgtg gttcagcgca tagatcgagc tggtcgagaa gggattcccg cccaccagca   2280
gcgtgtgata cgaaaacgcc tgccgcagat aggggtcctt gatgaaggtc gcgaccttgg   2340
catggaccga cttgtaggcc tccaacttca tcagcgcggg cgcggccttg agcatctggc   2400
ccagcttgag gaagggcacg gtgcccagct tgacgtagcc ctcctggtac acctcctcag   2460
cgtaatcacg gaagcggcgg tatccctcca ggtcgtccgg gttgaactgg gcgatctggc   2520
gttccagctg atcggcctcg ttcacgtaat cgaagacctt cccgcccggc cacatcagcc   2580
gatagaaggg cgagaccggc atcagcgtca cgtcgcgcgc catgtcctgc ccggtcaggg   2640
cccacagctc tttcagcgca tcggggtcgg tgatgacggt cgggcccgcg tcgaagagat   2700
ggccctgatc gtgccagaca taggcgcgcc cgccgggctt gtcccgggcc tcgaccaggg   2760
tggtggcgat gcccgcggac tgcaggcgga tggccagggc cagcccgcca aagcctgcgc   2820
cgatcacgat ggcggtcttg gccgcgggcg aatgggcgtt catgcgtttt ccttcagcag   2880
gggacgttcg ggcaggcagc ggatggccgt gccaagggga atgggaggct tgccggtcac   2940
gatgcgcagc tgatccgcca cgctcagccg gccggcatag aaccgttcga tcagtccatg   3000
cggcatgcgg tagaaccgct gcagcagggt atagcgccgg tcgggcgcgc agccgcggaa   3060
cagcatccgg ttcaaaaggc gcagaaagcg gtcgcggcgc gcccggtcga tcgcgtaatc   3120
gcggatggcg ccgcgcagcg cgtcggtgcc gggcggcccg gacagacccg ccaccacgtc   3180
cgccacctgt gccgcatagg gcagcgaata gccggtgacc ggatgaaaga ccccgcgcg    3240 cagtcccacg ggaacaggcc ccgccgcgtg atcggcccag aagcccgccg catcatgggc   3300
cagcgcgatg ggaaggatgc cgcgttcgcg ccggaccctcg gccccggtcc agccctgctg   3360
gcgggcatag tcgtgggacg ccgccgccag cgcgtcgtcg tccagatcgc cgccatcgga   3420
atagcgcgtg tcctcgatca ggatgcgcgt cggagagaag ggcagcagat agatgaagcg   3480
gtacccgtcc tgctgggtga cggtcgcgtc catgatcatc gggcggggca cgccgtgggg   3540
gcggtcggtc tcgatctcga cacccacgaa tttctggaaa cccacggtca gatgccgcga   3600
cggctgcgcg ccccgcccgt ccaggaccgc gcccgcctcg atccgggtgc cgcaggacag   3660
cgtcgccccc tgcgcatcca gcagggcgat gtcgctgtcc cagcggatct cggcgcccga   3720
ccggaccacc gcatccgcca gcgccgcccc gtccagcgac ccgtaaccgg tggccagccg   3780
ccgggcatgg cggggaaagc gcacctcctg gtcgggccag ttggcgcggc cagggccttt   3840
cagccgcgcc agccagtccg gcgacaggtc ggggtcgtgg caggaccagg tgtggccgtc   3900
tgacggtcct gcggcatggt ccagcagcag cacgcgcagg tcgggccgcg ccgcgcgcag   3960
cgccagggcg atcagcccgt tggcaaggcc cgccctgcc agcagcacgt catgggtcac   4020
gtgcgctcct gcgcctcggc ccgcagcacg cccgacatct tcaggtcctg cttcagcttg   4080
tcgaccgggg gcgcatagat gaagccgaag ctgacgcaat ggtcgcgccc ctcgaccgca   4140
```

```
tggtgcaggc ggtgggcctg atacaggcgt ctggcatagc ccttgcgcgg gatataacgg    4200
aacggccagc gctgatgcac cagcccgtca tgcaggacga aatagatcag cccatagaca    4260
gtcatgccca aggcgatcca ccacaggacc ggcgcccaga tccagcccac cgtgaacagc    4320
accgtggcga tcaccgcaaa gaccaggccg tacaggtcgt tcttttccag cgcgtggtcg    4380
tgttcctcgt ggtgggactt gtgccagccc agcccagggg gccgtgcat gatccagcgg     4440 tggacggaat aggccgtcaa ctccatcacc agcacggtgg cgacgacgat caggaaattg    4500
gtcatgcggt gtccccttg gtgcgggtgc tgggcaggcg ccaccacggc accgtcgggt     4560
gcaggtggtg ttcgtgatga taaccgccaa agtgaaagca ggtcagcagc gacacggggt    4620
cgctgatccg cgacgaccgc gcattgtggc ggtccgggaa cgcgtcgtgg ccggggcggt    4680
gcggcagcca ggtgccgaac acgaacagct ggatcgacgc caggatcgac ggcagcggcc    4740
agaagaccac gtacatccag cgatccccaa ggatcagcgc atagaccgtc acgatgacgg    4800
gcagcagcag cccctcgcgc cagccgaaat aggtgccgat gaagcgggcg taccagcgga    4860
ccgggccgcc atggtcgaaa tcggggtcgt cgtcggttcc ggcatggcgg tgatgggcca    4920
tgtgcttgac gatcatcttg cgccacgaaa atcggcata cagccacagg acaagctggc     4980
ccatcgccgc attggcgcgc ggacgccccg gcaccaccga cccgtgcatc gcgtcatgcg    5040
cgatgatgaa caatccgacc gacagccagg tcagccccag gaaatttgcg atcgccagga    5100
tgggatgcgc cgctgcgtcc agaaaccaca gcgcatgcac atgcagggcc agccaagcgg    5160
cgatgatgcc gcccgagacg atcaggctgg tgcggtcag atctgccttg ggcagggcat     5220
gtgcgctcat cttgtccccc ggaccggcga tccgcgcaga ctacagtccc gcatcgccgg    5280
tttccatccc cgttgcttgc gaccattggc caccgcgcc aggcaccagc aaaggcgcgc     5340
ggcgcagcgc cgcaaggtcg ccggatccta gatgcttgac aatccgggtg acgcggccga    5400
cctgcgccgc gccgcgcgcc ggacgatcct ggccgatcat gatgcggcgc gggtgtttcc    5460
ggccaaggat gcctggctgc gcgcggccat cggcgcgccg gtccactgac cttgttggac    5520
aaattgccgc gcgaccccgc gtcgccgtcg aaaaggctcg caatcgggcg tgaaccgttc    5580
caacatgggg actgttgacg gtggatgacg ggtcacgggg tgccgccccg gcctgacctt    5640
cccgccaggt cagaacccca gcgcgagggc actgatgaga cgagacgtca acccgatcca    5700
cgccacccct ctgcagacca gacttgagga gatcgcccag ggattcggtg ccgtgtcgca    5760
gccgctcggc gcggccatga gccatggcgc gctgtcgtcg ggcaagcggt tccgcggcat    5820
gctgatgctg cttgcggcag aggcctcggg cggggtctgc gacacgatcg tcgacgccgc    5880
ctgcgcggtc gagatggtgc atgccgcatc gctgatcttc gacgacctgc cctgcatgga    5940
cgatgccggg ctgcgccgcg gccagtccgc gacccatgtg cgcatggcg aaagccgcgc     6000 cgtgctgggc ggcatcgccc tgatcaccga ggcgatggcc ctgctggccg gtgcgcgcgg    6060
cgcgtcgggc acgggcggg cgcagctggt gcggatcctg tcgcggtccc tggggccgca     6120
gggcctgtgc gccggccagg acctggacct gcacgcggcc aagaacggcg cggggtcga    6180 acaggaacag gacctgaaga ccggcgtgct gttcatcgcc gggctggaga cgctggccgt    6240
gatcaaggag ttcgacgccg aggagcagac ccagatgatc gactttggcc gtcagctggg    6300
ccgggtgttc cagtcctatg acgacctgct ggacgtcgtg ggcgaccagg cggcgcttgg    6360
caaggatacc ggtcgcgatg ccgcggcccc cggcccgcgg cgcggccttc tggccgtgtc    6420
agacctgcag aacgtgtccc gccactatga ggccagccgc gcccagctgg acgcgatgct    6480
```

```
gcgcagcaag cgccttcagg ctccggaaat cgcggccctg ctggaacggg ttctgcccta    6540
cgccgcgcgc gcctaggcgt gatgagctcc ca                                  6572
```

<210> SEQ ID NO 13
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13

```
gcggatccgg cgaccttgcg gcgctg                                         26
```

<210> SEQ ID NO 14
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14

```
cgggatcctg tcgcggtccc tgggg                                          25
```

<210> SEQ ID NO 15
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15

```
cgggatccgc agggcgatca gcccgttggc aagg                                34
```

<210> SEQ ID NO 16
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16

```
ctagtctaga tgcttgacaa tccgggtgac gcgg                                34
```

<210> SEQ ID NO 17
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17

```
tgggagctca tcacgcctag gcgcgcgcgg cgtag                               35
```

<210> SEQ ID NO 18
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18

```
ctagtctaga gccggtccac tgaccttgtt ggac                                34
```

<210> SEQ ID NO 19
<211> LENGTH: 138
<212> TYPE: DNA
<213> ORGANISM: Paracoccus sp.

<400> SEQUENCE: 19

```
ggatccggcg accttgcggc gctgcgccgc gcgcctttgc tggtgcctgg gccgggtggc     60
caatggtcgc aagcaacggg gatggaaacc ggcgatgcgg gactgtagtc tgcgcggatc   120
gccggtccgg gggacaag                                                 138
```

<210> SEQ ID NO 20
<211> LENGTH: 302
<212> TYPE: DNA
<213> ORGANISM: Paracoccus sp.

<400> SEQUENCE: 20

```
tgcttgacaa tccgggtgac gcggccgacc tgcgccgcgc cgcgcgccgg acgatcctgg     60
ccgatcatga tgcggcgcgg gtgtttccgg ccaaggatgc ctggctgcgc gcggccatcg   120
gcgcgccggt ccactgacct tgttggacaa attgccgcgc gaccccgcgt cgccgtcgaa   180
aaggctcgca atcgggcgtg aaccgttcca acatggggac tgttgacggt ggatgacggg   240
tcacggggtg ccgccccggc ctgaccttcc cgccaggtca aaccccagc gcgagggcac   300 tg                                                                  302
```

<210> SEQ ID NO 21
<211> LENGTH: 178
<212> TYPE: DNA
<213> ORGANISM: Paracoccus sp.

<400> SEQUENCE: 21

```
gccggtccac tgaccttgtt ggacaaattg ccgcgcgacc ccgcgtcgcc gtcgaaaagg     60
ctcgcaatcg ggcgtgaacc gttccaacat ggggactgtt gacggtggat gacgggtcac   120
ggggtgccgc cccggcctga ccttcccgcc aggtcagaac cccagcgcga gggcactg     178
```

<210> SEQ ID NO 22
<211> LENGTH: 34
<212> TYPE: DNA
<213> ORGANISM: Artificial Sequence
<220> FEATURE:
<223> OTHER INFORMATION: Description of Artificial Sequence: Synthetic
      construct oligonucleotide

<400> SEQUENCE: 22

```
tcatctagag gtaccatatg aagcttgagc tcct                                34
```

<210> SEQ ID NO 23
<211> LENGTH: 29
<212> TYPE: DNA
<213> ORGANISM: Artificial Sequence
<220> FEATURE:
<223> OTHER INFORMATION: Description of Artificial Sequence: Synthetic
      construct oligonucleotide

<400> SEQUENCE: 23

```
gagctcaagc ttcatatggt acctctaga                                      29
```

<210> SEQ ID NO 24

```
<211> LENGTH: 1360
<212> TYPE: DNA
<213> ORGANISM: Paracoccus sp.

<400> SEQUENCE: 24
cgagcgagac cttcgggtct agcggcggac gggtgagtaa cgcgtgggaa cgtgcccttc      60
tctacggaat agccccggga aactgggagt aataccgtat acgcccttg ggggaaagat      120 ttatcggaga aggatcggcc cgcgttggat taggtagttg gtggggtaat ggcccaccaa      180
gccgacgatc catagctggt ttgagaggat gatcagccac actgggactg agacacggcc      240
cagactccta cgggaggcag cagtgggaa tcttagacaa tggggcaac cctgatctag       300 ccatgccgcg tgagtgatga aggccttagg gttgtaaagc tctttcagct gggaagataa      360
tgacggtacc agcagaagaa gccccggcta actccgtgcc agcagccgcg gtaatacgga      420
gggggctagc gttgttcgga attactgggc gtaaagcgca cgtaggcgga ctggaaagtc      480
agaggtgaaa tcccagggct caaccttgga actgcctttg aaactatcag tctggagttc      540
gagagaggtg agtggaattc cgagtgtaga ggtgaaattc gtagatattc ggaggaacac      600
cagtggcgaa ggcggctcac tggctcgata ctgacgctga ggtgcgaaag cgtgggagc      660 aaacaggatt agataccctg gtagtccacg ccgtaaacga tgaatgccag acgtcggcaa      720
gcatgcttgt cggtgtcaca cctaacggat taagcattcc gcctggggag tacggtcgca      780
agattaaaac tcaaaggaat tgacggggcc cgcacaagc ggtggagcat gtggtttaat       840
tcgaagcaac gcgcagaacc ttaccaaccc ttgacatggc aggaccgctg gagagattca      900
gctttctcgt aagagacctg cacacaggtg ctgcatggct gtcgtcagct cgtgtcgtga      960
gatgttcggt taagtccggc aacgagcgca acccacgtcc ctagttgcca gcattcagtt     1020
gggcactcta tggaaactgc cgatgataag tcggaggaag gtgtggatga cgtcaagtcc     1080
tcatggccct tacgggttgg gctacacacg tgctacaatg gtggtgacag tgggttaatc     1140
cccaaaagcc atctcagttc ggattgtcct ctgcaactcg agggcatgaa gttggaatcg     1200
ctagtaatcg cggaacagca tgccgcggtg aatacgttcc cgggccttgt acacaccgcc     1260
cgtcacacca tgggagttgg ttctacccga cgacgctgcg ctaaccttcg gggggcaggc     1320
ggccacggta ggatcagcga ctggggtgaa gtcgtaacaa                            1360
```

The invention claimed is:

1. A method of preparing a carotenoid comprising the steps of:

culturing a cell transformed with a DNA chain having a DNA sequence selected from the group consisting of the following (a) to (f) and having a DNA sequence described in SEQ ID NO: 19, SEQ ID NO: 20, or SEQ ID NO: 21 or a cell transformed with a vector having a DNA sequence selected from the group consisting of the following (a) to (f) in an appropriate culture condition and having a DNA sequence described in SEQ ID NO: 19, SEQ ID NO: 20, or SEQ ID NO: 21, and isolating the carotenoid from the cell or a culture medium:

(a) a DNA sequence encoding a polypeptide having an enzymatic activity of an enzyme that is found in *Paracoccus* sp. strain MBIC1143 and converts a methylene group at 4 position in β-ionone ring into a keto group (crtW), described in SEQ ID NO: 2;

(b) a DNA sequence encoding a polypeptide having an enzymatic activity of an enzyme that is found in *Paracoccus* sp. strain MBIC1143 and adds one hydroxyl group to a carbon at 3-position of 4-keto-β-ionone ring and/or at 3-position of β-ionone ring (crtZ), described in SEQ ID NO: 3;

(c) a DNA sequence encoding a polypeptide having an enzymatic activity of an enzyme that is found in *Paracoccus* sp. strain MBIC1143 and converts lycopene into β-carotene (crtY), described in SEQ ID NO: 4;

(d) a DNA sequence encoding a polypeptide having an enzymatic activity of an enzyme that is found in *Paracoccus* sp. strain MBIC1143 and converts phytoene into lycopene (crtI), described in SEQ ID NO: 5;

(e) a DNA sequence encoding a polypeptide having an enzymatic activity of prephytoene synthase that is found in *Paracoccus* sp. strain MBIC1143 (crtB), as described in SEQ ID NO: 6; and (f) a DNA sequence encoding a polypeptide having an enzymatic activity of geranylgeranyl diphosphate synthase that is found in *Paracoccus* sp. strain MBIC1143 (crtE), as described in SEQ ID NO: 7.

2. A DNA chain having a promoter activity in a marine bacterium, described in SEQ ID NO: 20.

3. A DNA chain having a promoter activity in a marine bacterium, described in SEQ ID NO: 21.

4. A continuous oligonucleotide sequence selected from the group consisting of combinations of the DNA chain according to claim 1 and the DNA chain described in SEQ ID NO: 19, SEQ ID NO: 20, or SEQ ID NO: 21.

5. A plasmid vector comprising the oligonucleotide according to claim 4.

6. A cell transformed with the plasmid vector according to claim 5.

7. A method of producing a carotenoid, comprising:
   culturing under a condition that enables expression of a polypeptide encoded by the DNA chain sequence of the plasmid vector according to claim 5; and
   isolating the carotenoid from a cell or a culture medium of cell.

8. The method according to claim 7, wherein the cell is a prokaryotic host cell.

9. The method according to claim 7, wherein the cell is a marine bacterium.

10. The method according to claim 7, wherein the cell is a bacterium in which 16S rRNA has a DNA base sequence that has a 97% or higher homology to the DNA base sequence of SEQ ID NO: 24.

11. A method of preparing a desired carotenoid or a carotenoid mixture, comprising:
   culturing the cell according to claim 6 under an appropriate culture condition;
   isolating the desired carotenoid or a carotenoid mixture from the cell or culture medium; and
   separating a single carotenoid from other possibly coexisting carotenoids when such a single carotenoid is desired.

12. A method of preparing a food or feed composition, comprising:
   executing the method according to claim 11, and then
   adding the carotenoid or carotenoid mixture to food or feed.

13. The method according to claim 9, wherein the marine bacterium is *Paracoccus* sp.

14. The method according to claim 8, wherein the prokaryotic host cell is *Escherichia coli* or *Bacillus*.

* * * * *